(12) United States Patent
Ragade

(10) Patent No.: US 7,837,470 B2
(45) Date of Patent: Nov. 23, 2010

(54) MOVABLE MANDIBLE ARTICULATOR

(76) Inventor: Anil Sudhakar Ragade, Plot No. 461, Sector No. 25, Pradhikaran, Nigidi, Pune 411044 (IN)

( * ) Notice: Subject to any disclaimer, the term of this patent is extended or adjusted under 35 U.S.C. 154(b) by 223 days.

(21) Appl. No.: 12/196,110

(22) Filed: Aug. 21, 2008

(65) Prior Publication Data
US 2009/0325121 A1 Dec. 31, 2009

(51) Int. Cl.
*A61C 11/00* (2006.01)
(52) U.S. Cl. .............. 433/57; 433/59; 433/62; 433/64
(58) Field of Classification Search .............. 433/57–67
See application file for complete search history.

(56) References Cited

U.S. PATENT DOCUMENTS

| | | | | |
|---|---|---|---|---|
| 566,950 A | * | 9/1896 | Walker | 433/55 |
| 1,319,737 A | * | 10/1919 | Wadsworth | 433/59 |
| 1,598,535 A | * | 8/1926 | Lentz | 433/61 |
| 2,219,559 A | * | 10/1940 | Lentz | 433/55 |
| 2,608,761 A | * | 9/1952 | Scott | 433/56 |
| 2,720,026 A | * | 10/1955 | Miller | 433/37 |
| 3,905,112 A | * | 9/1975 | Swanson | 433/57 |
| 3,908,271 A | * | 9/1975 | Derda et al. | 433/58 |
| 4,189,837 A | * | 2/1980 | Stele | 433/57 |
| 4,391,589 A | * | 7/1983 | Monfredo et al. | 433/63 |
| 4,496,319 A | * | 1/1985 | Steinbock | 433/57 |
| 4,505,674 A | * | 3/1985 | Edwardson | 433/59 |
| 5,026,282 A | * | 6/1991 | Koike | 433/62 |

* cited by examiner

*Primary Examiner*—John J Wilson
(74) *Attorney, Agent, or Firm*—Egbert Law Offices PLLC

(57) ABSTRACT

The present invention relates to an articulator capable of completely and faithfully reproducing movements of a mandibular cast and maxillary cast. The articulator introduces a suspended mandibular member, the mandible being similar to that of in human beings. The mandible is suspended from the condyles in the glenoid fossa of the tempero mandibular joint. The articulator and the mandibular member are suspended between the maxillary member and the base representing the feet or base in a human. The articulator has a mechanism for anterior incisal guidance by providing incisal pins attached to the mandibular member. The incisal pin attached to the mandibular member creates the anterior guidance on an incisal table resting on the base. The articulator creates the possibility of the condyle executing pure rotary movement in the centric position until a vertical opening between the upper and lower jaws.

9 Claims, 35 Drawing Sheets

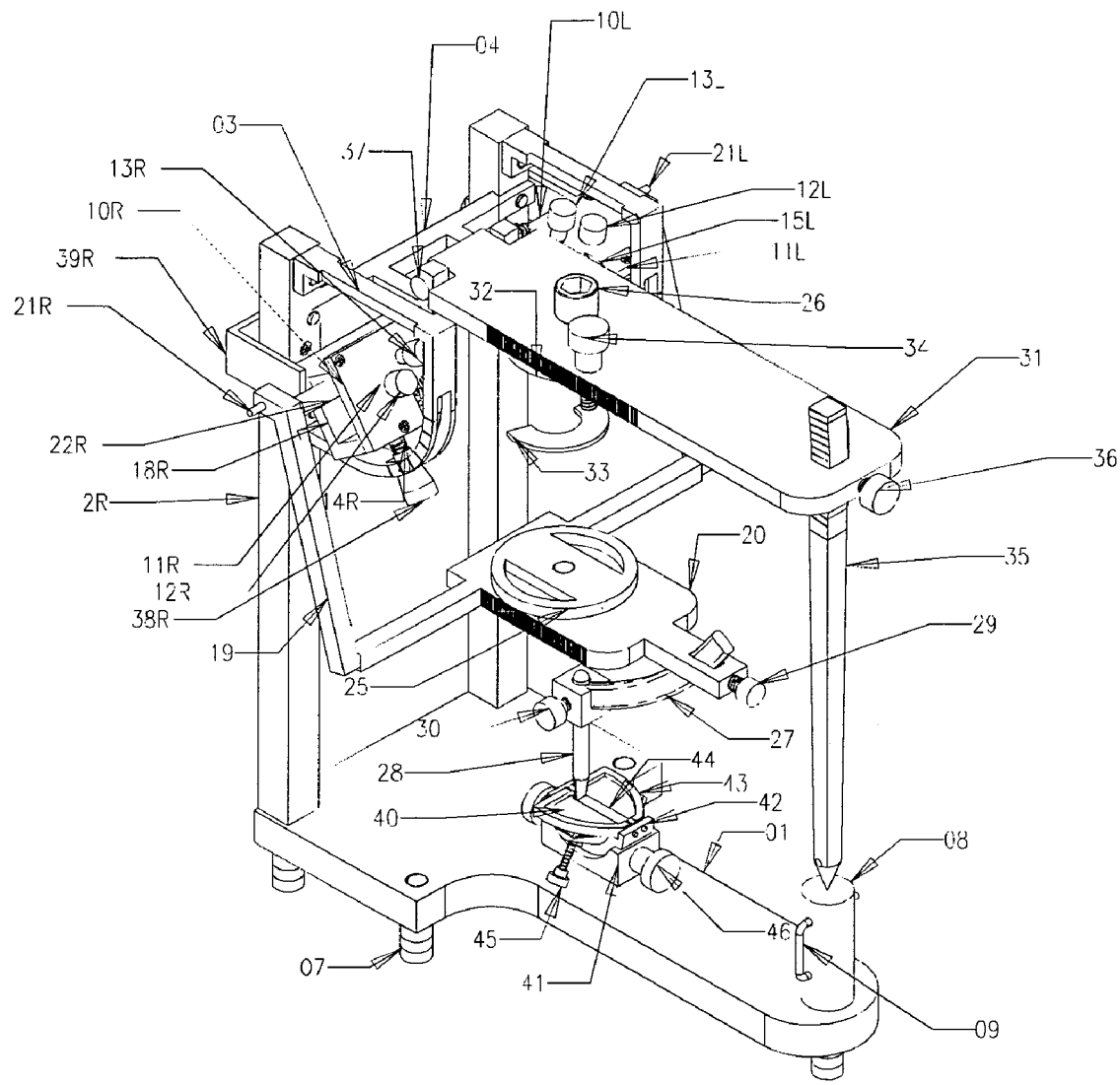
FIG. NO. 1

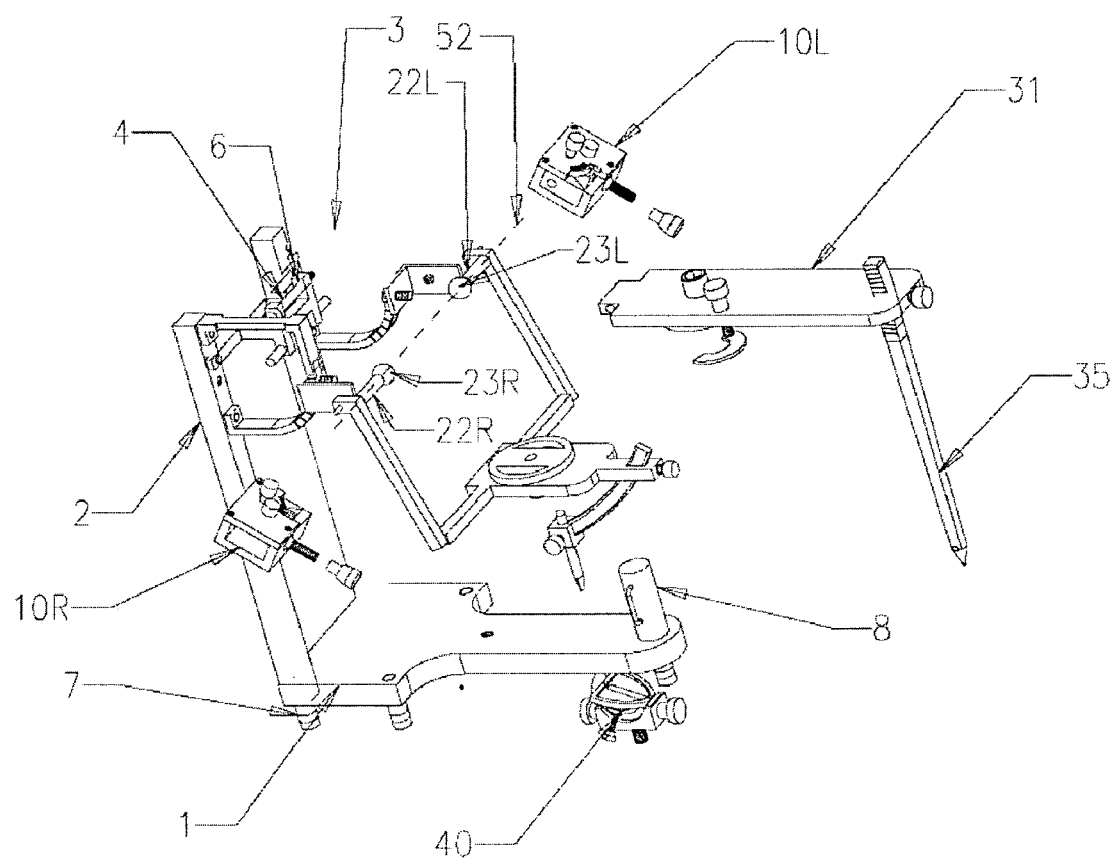
FIG. NO. 2

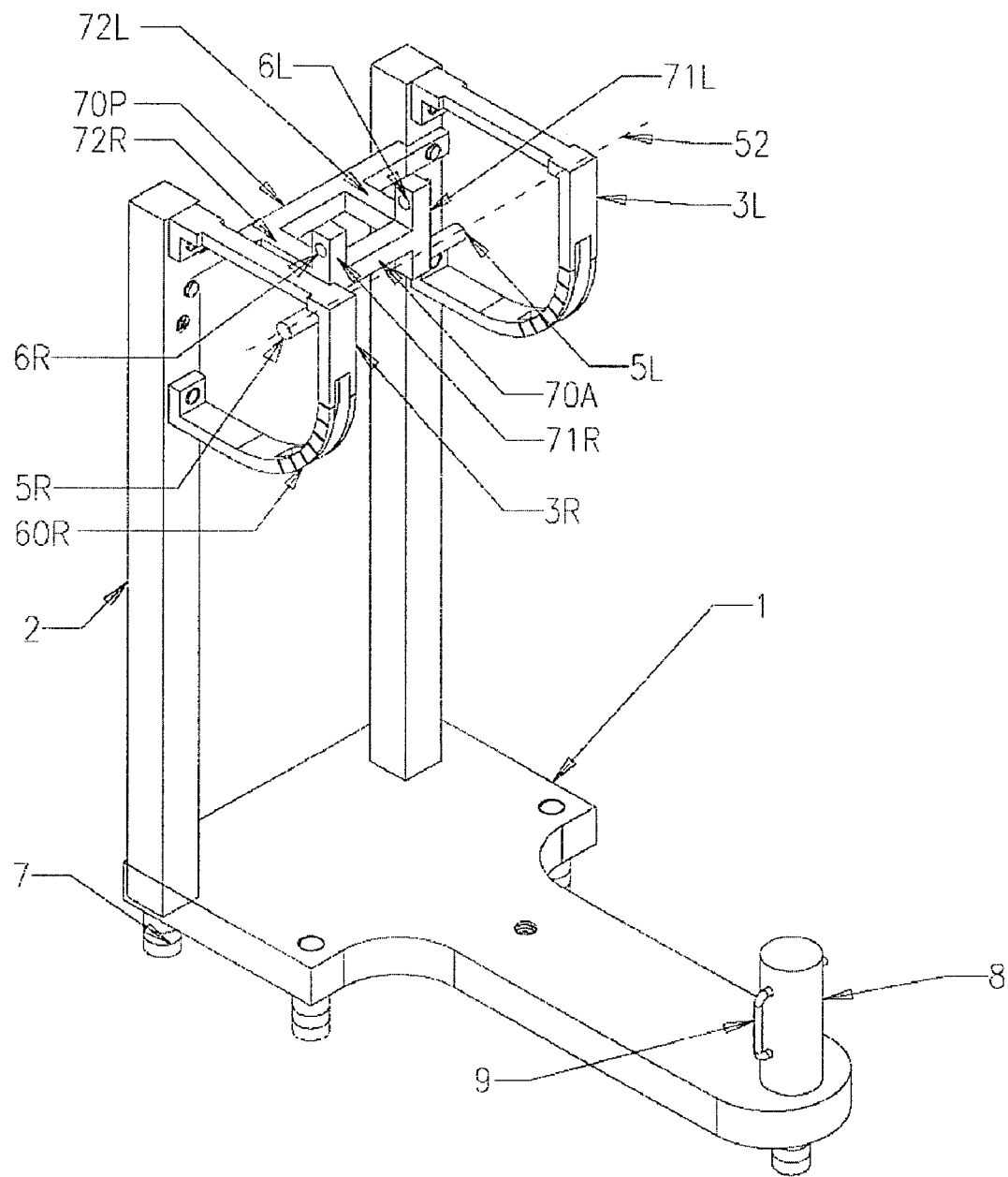
FIG. NO. 3

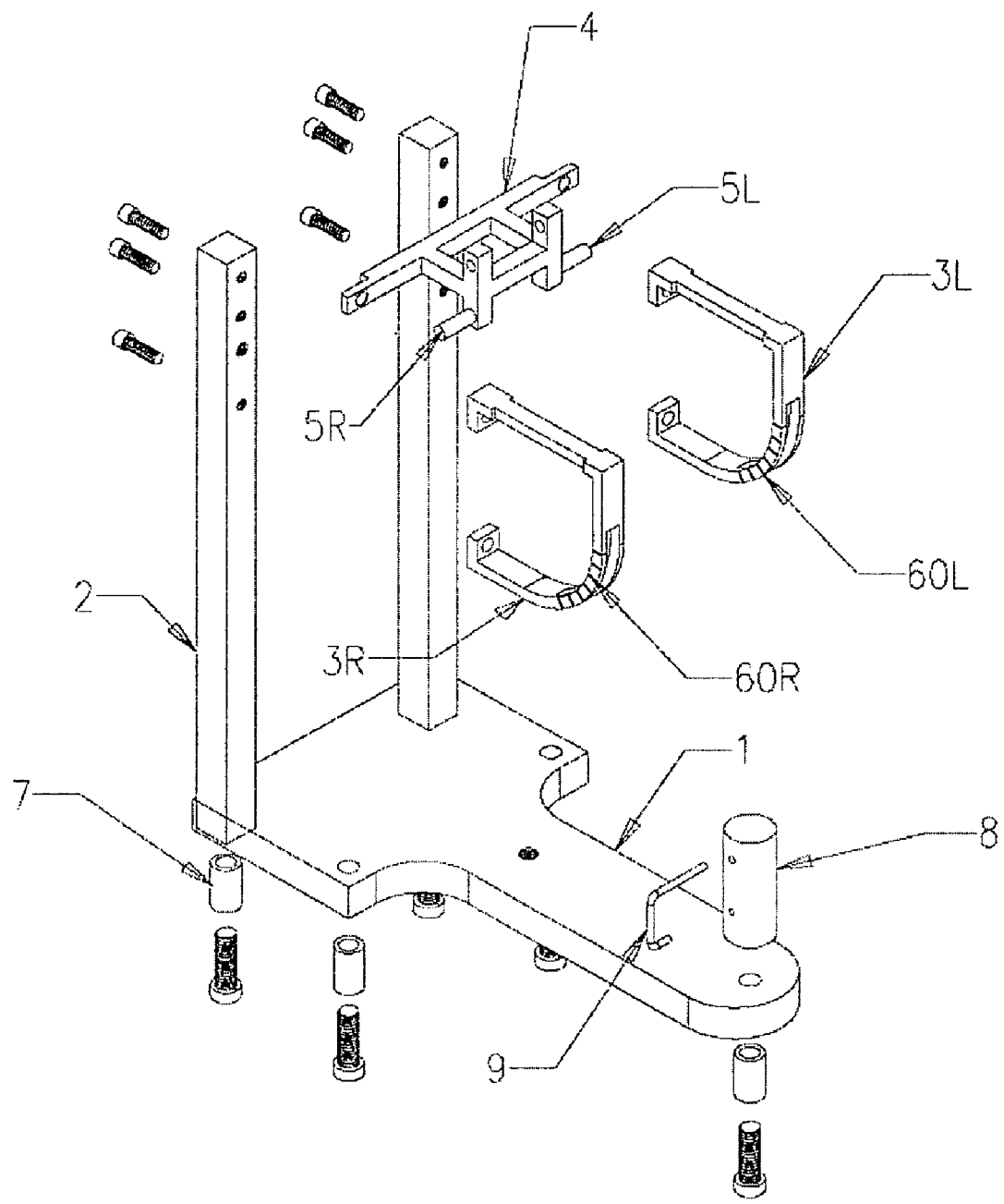
FIG. NO. 4

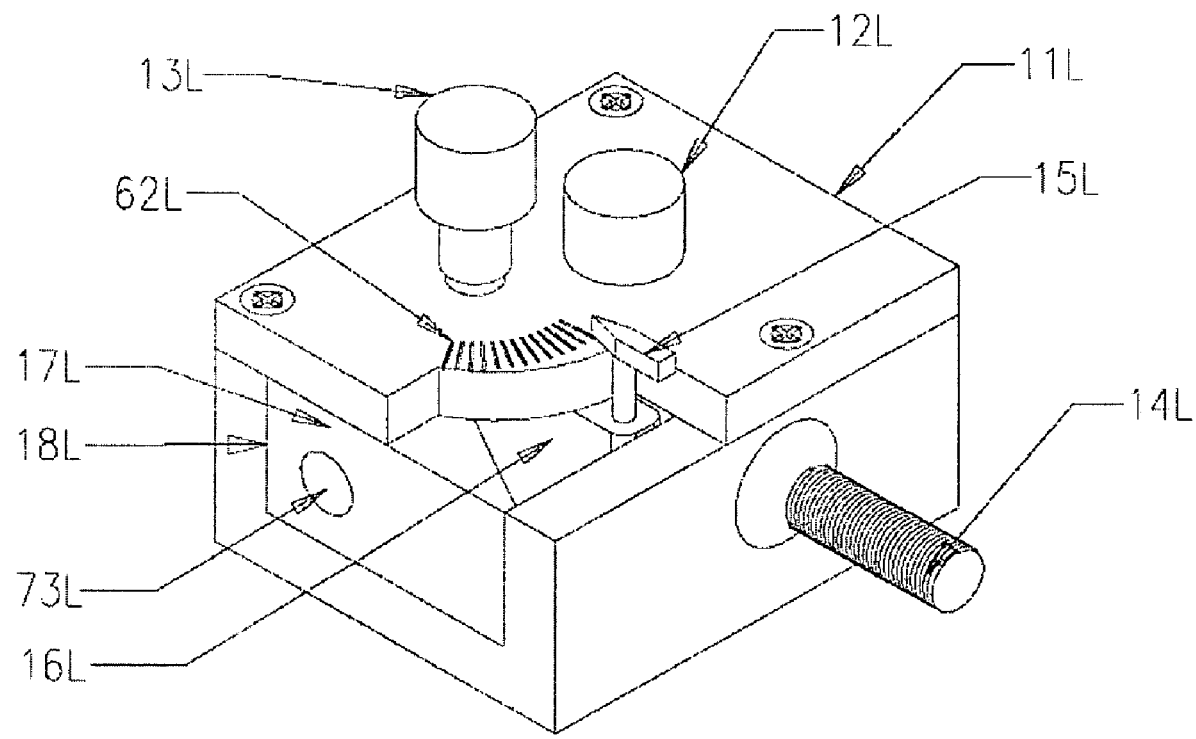
FIG. NO. 5

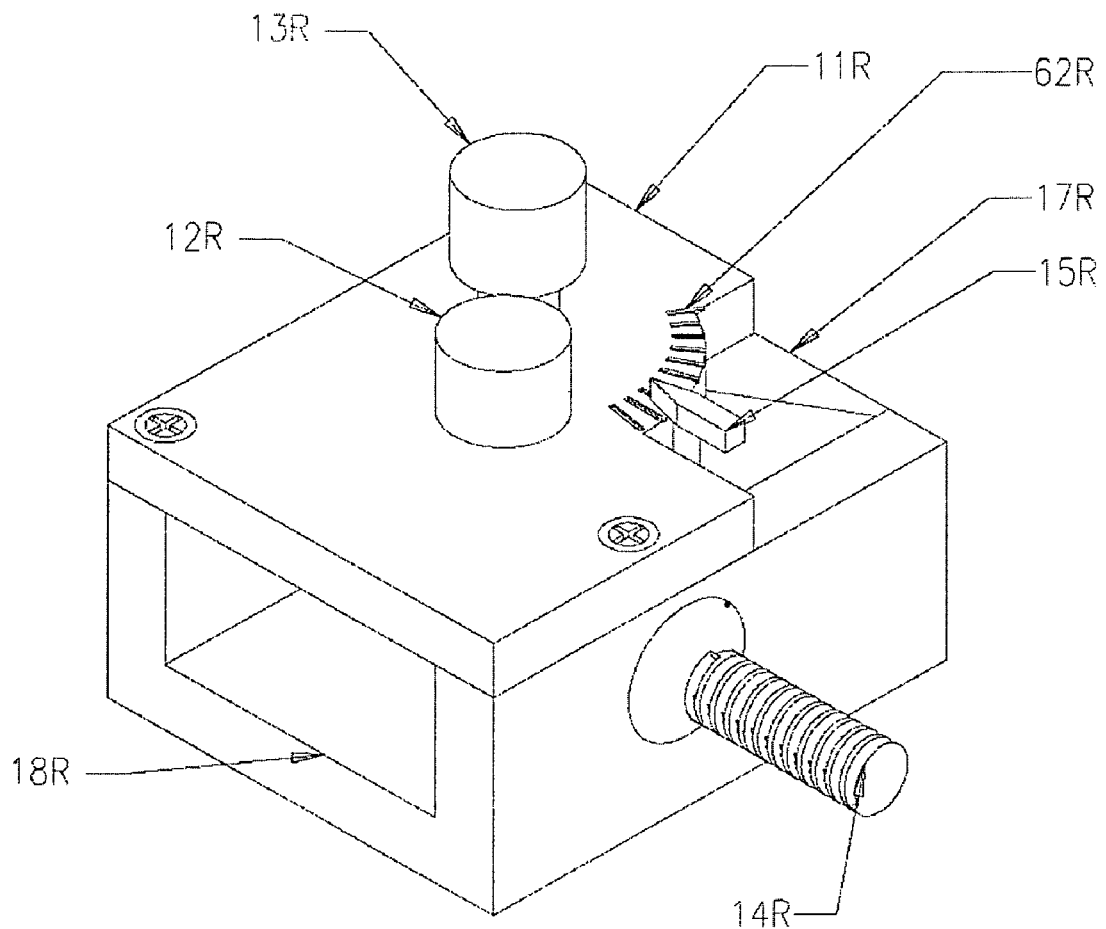
FIG. NO. 6

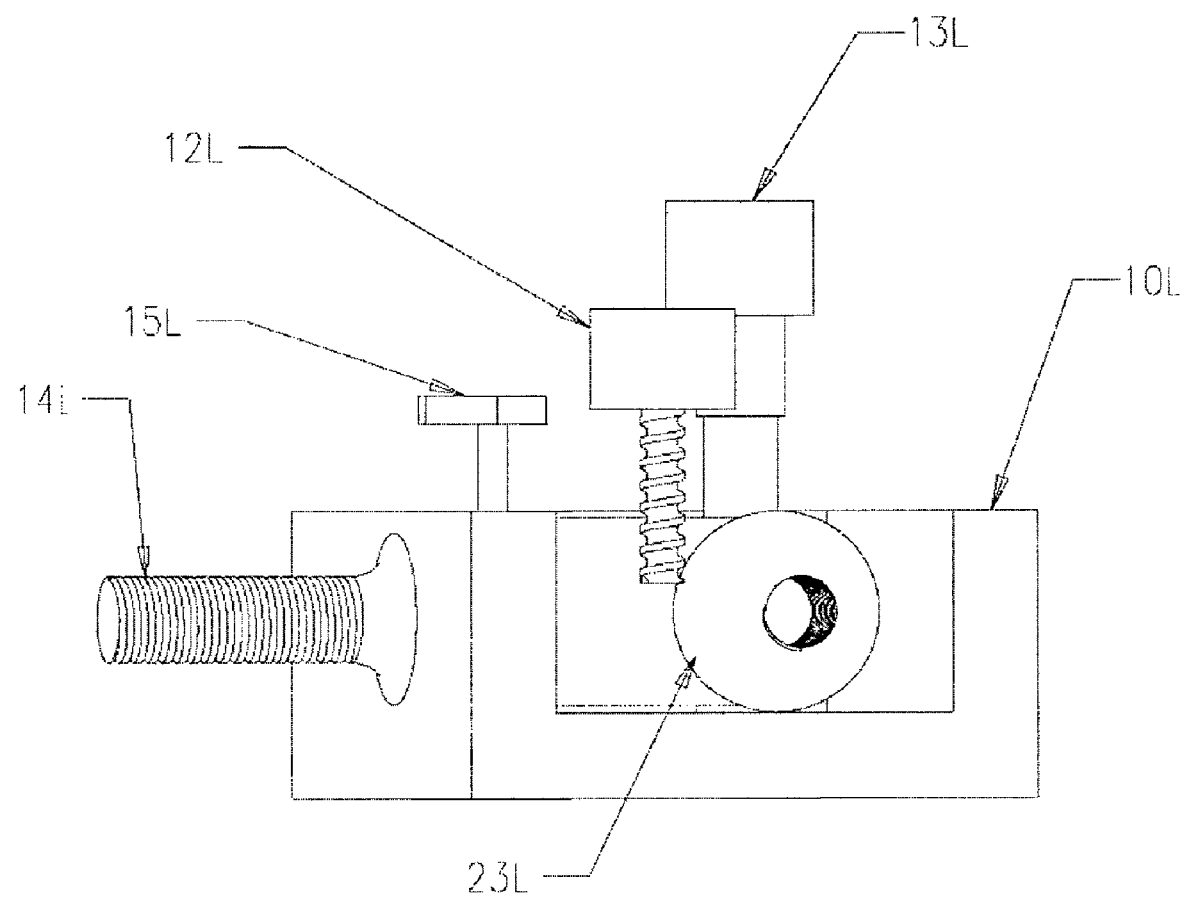
FIG. NO. 7

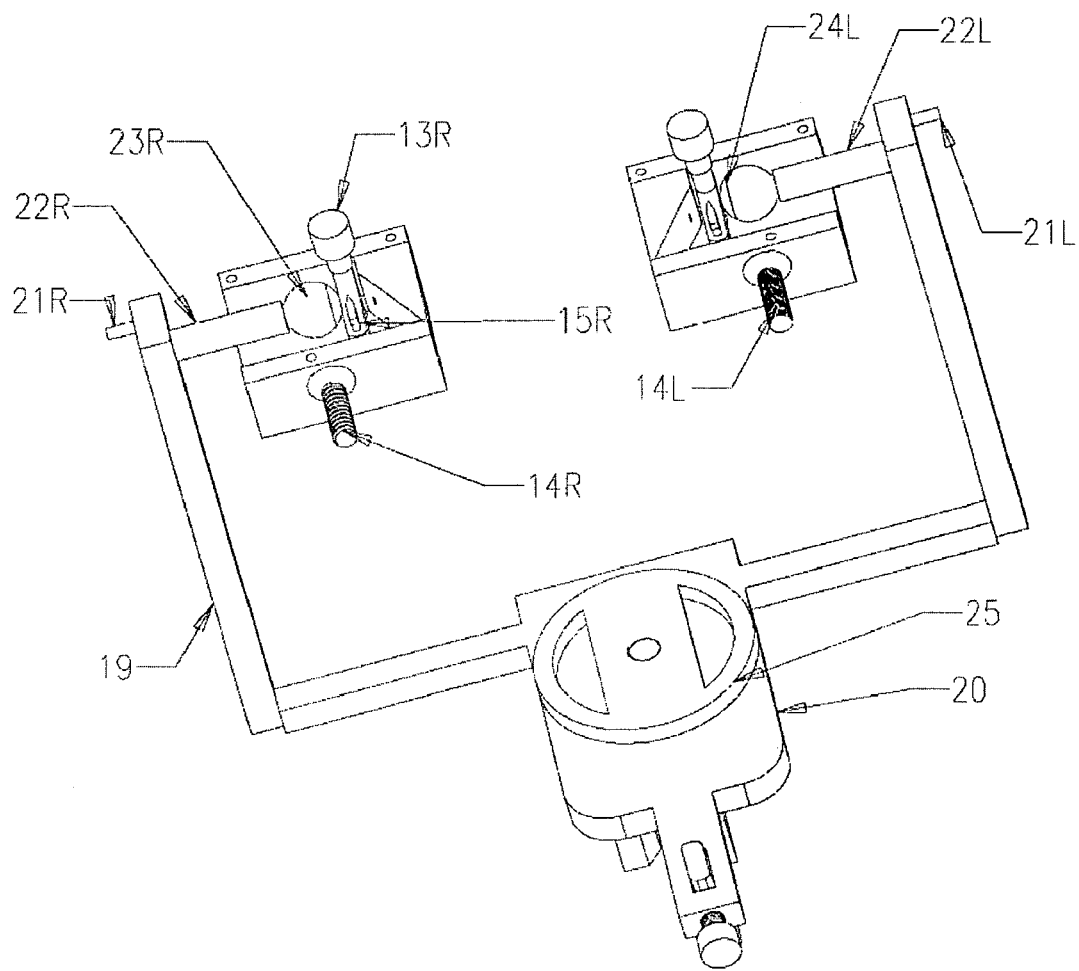
FIG. NO. 8

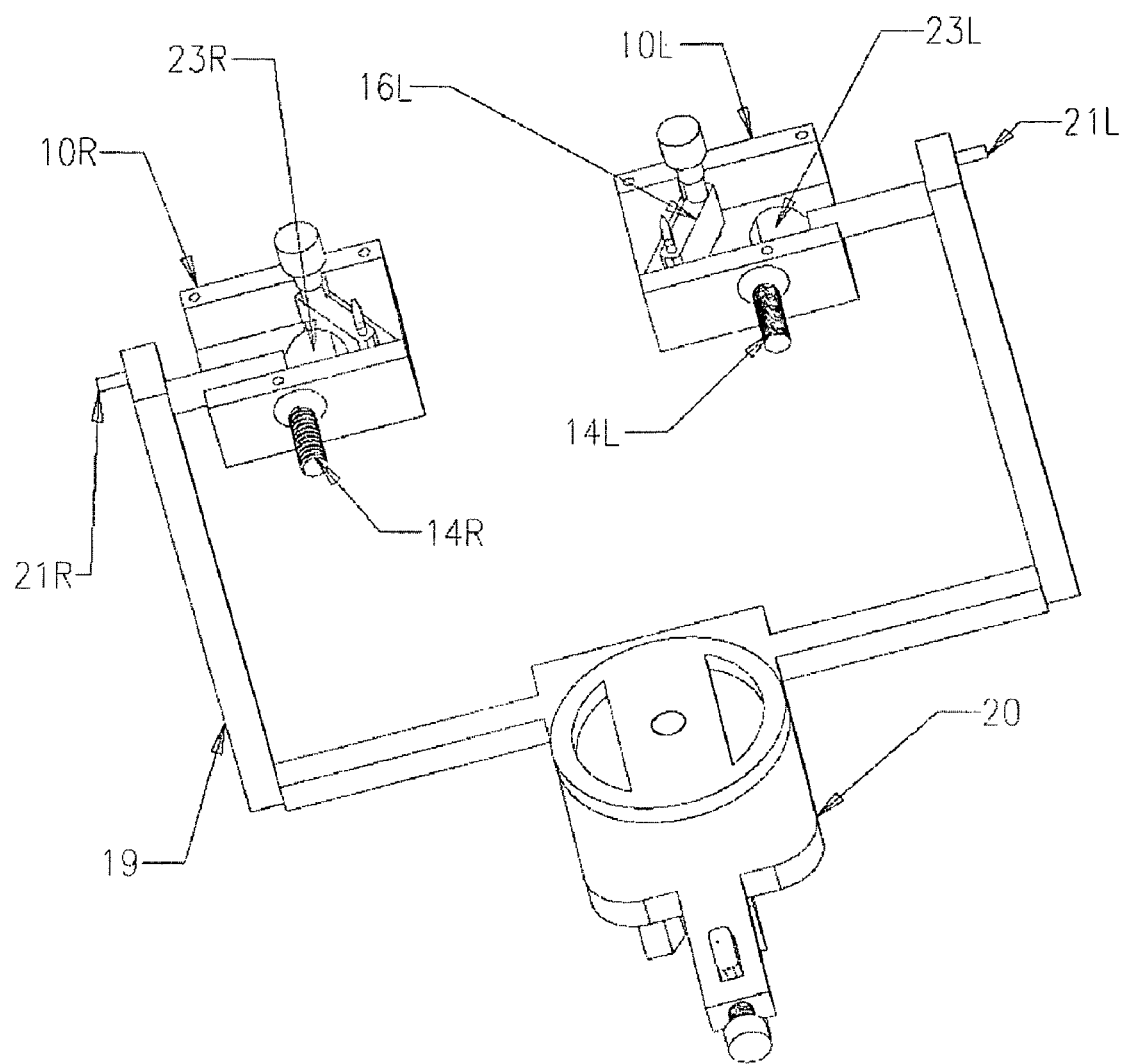
FIG. NO. 9

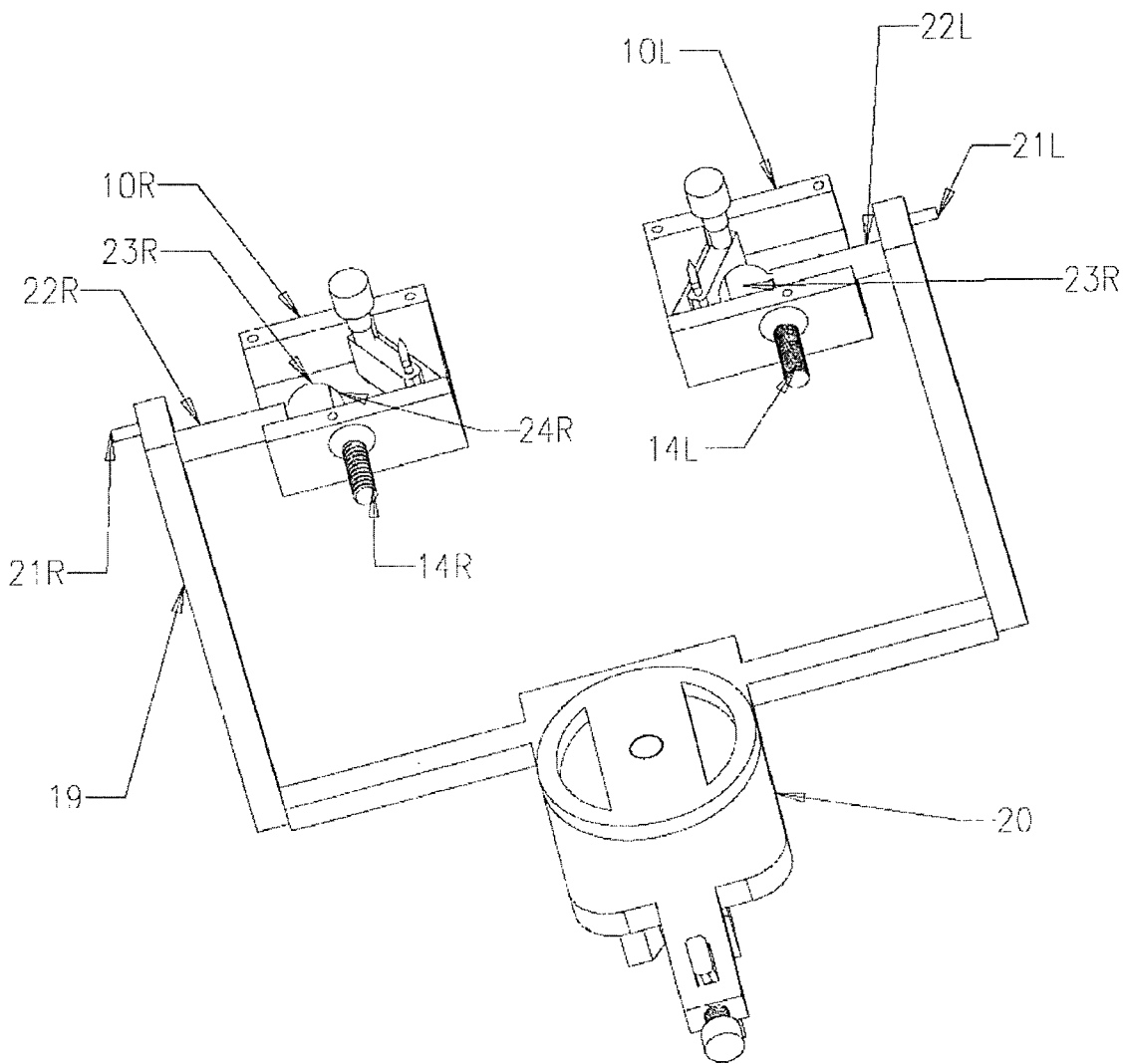
FIG. NO. 10

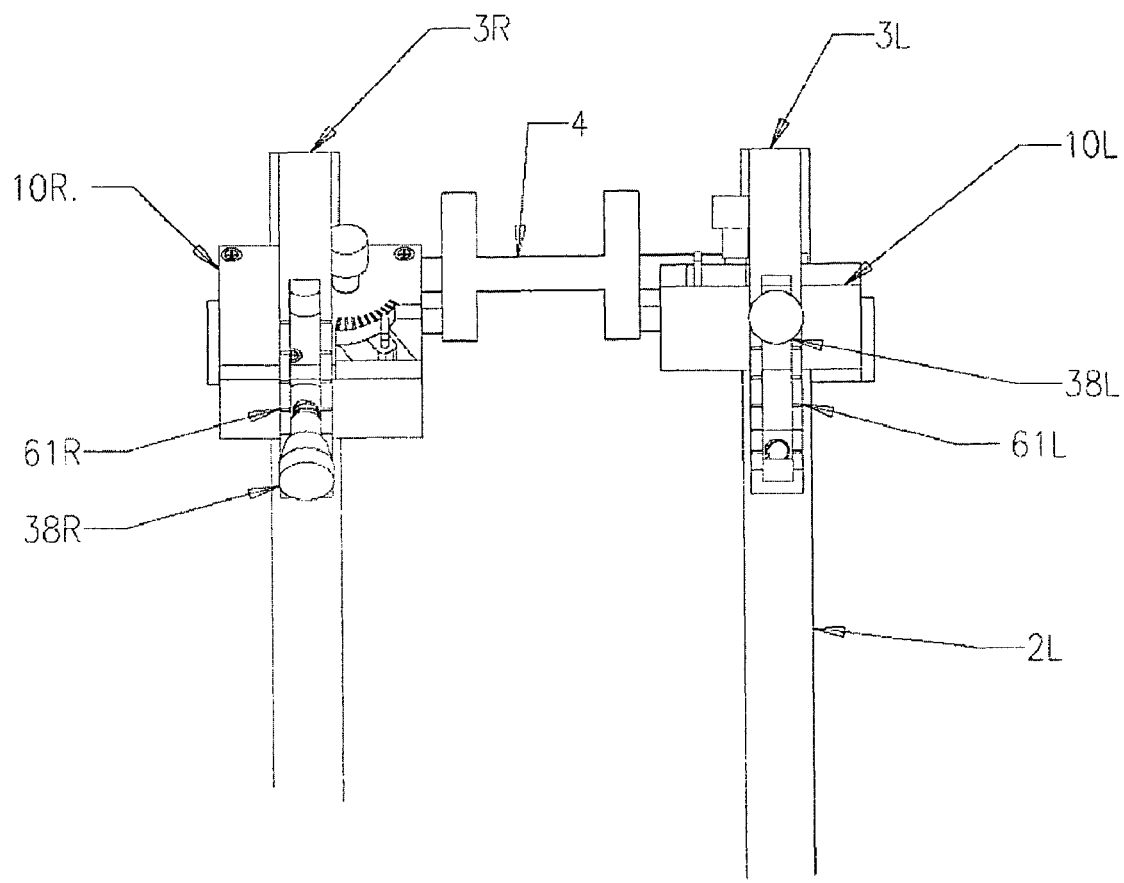
FIG. NO. 11

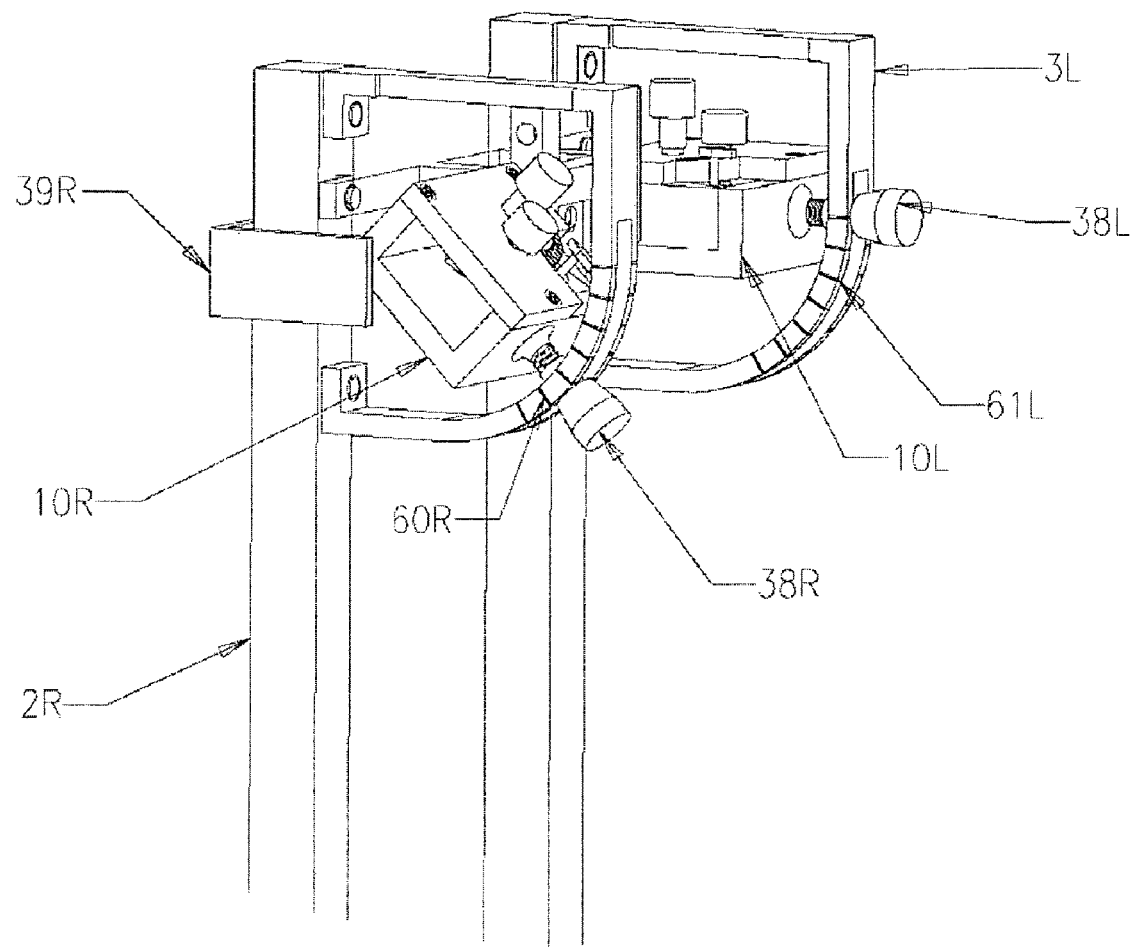
FIG. NO. 12

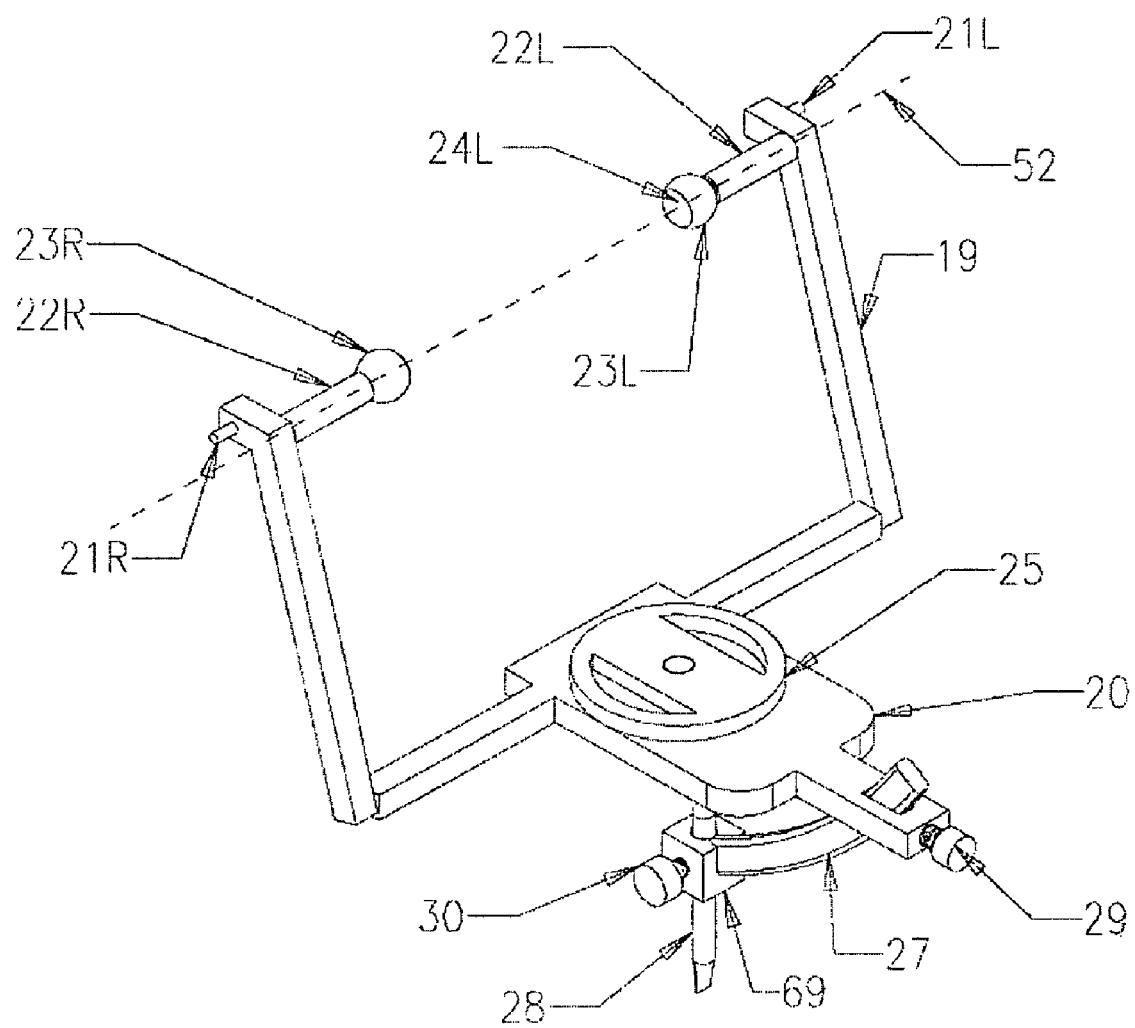
FIG. NO. 13

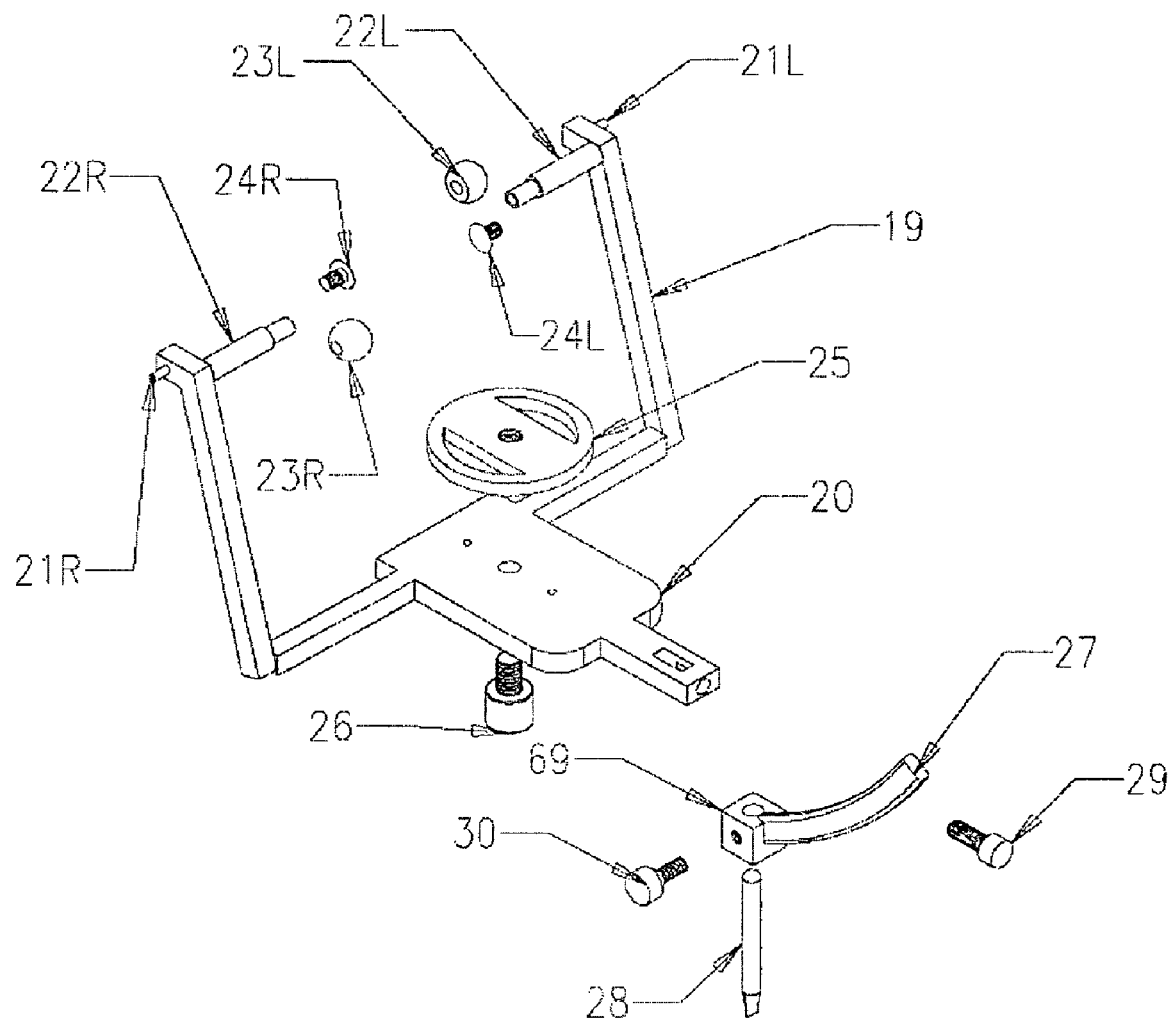
FIG. NO. 14

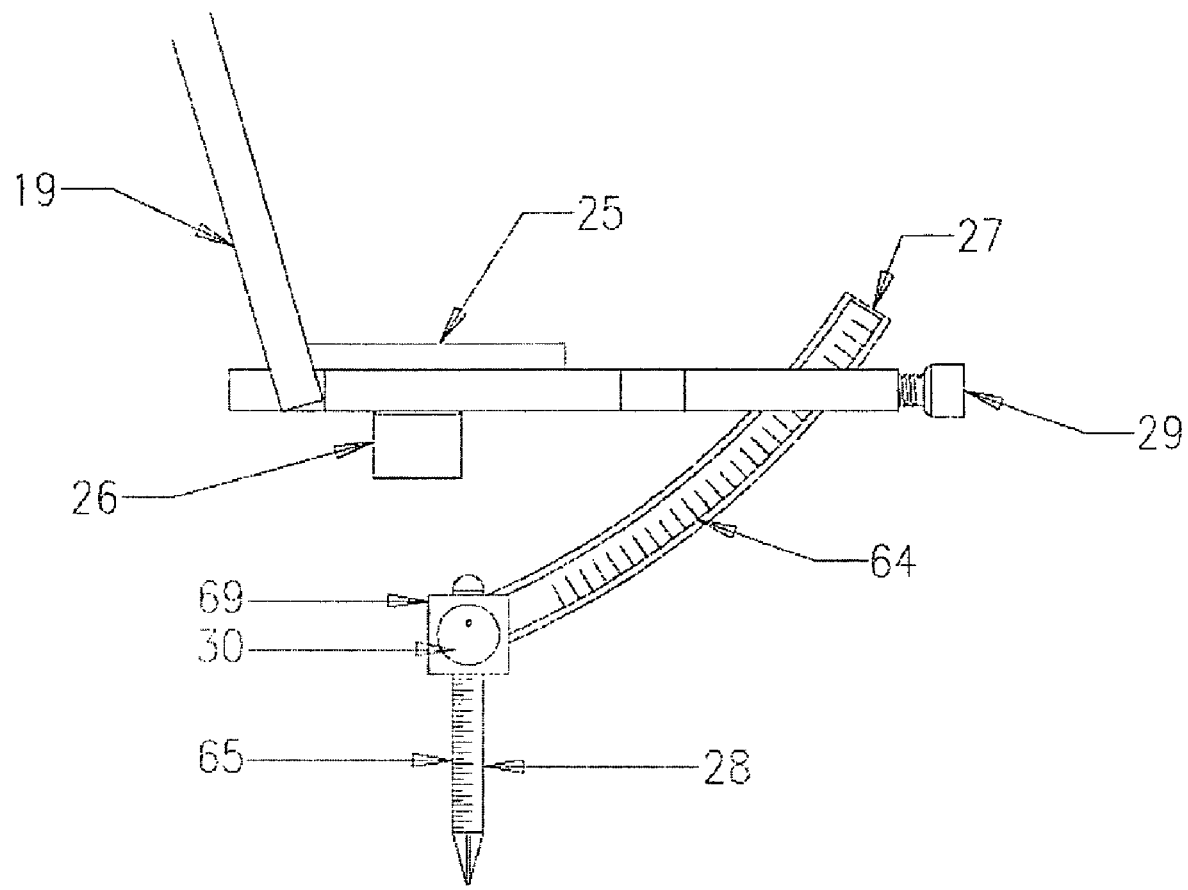
FIG. NO. 15

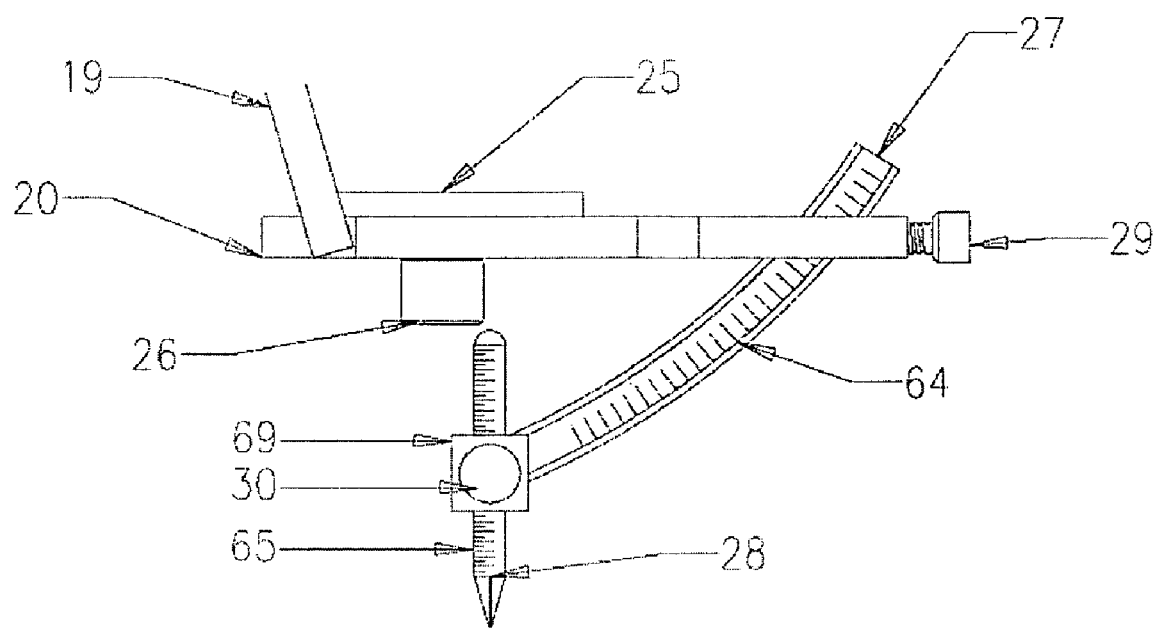
FIG. NO. 16

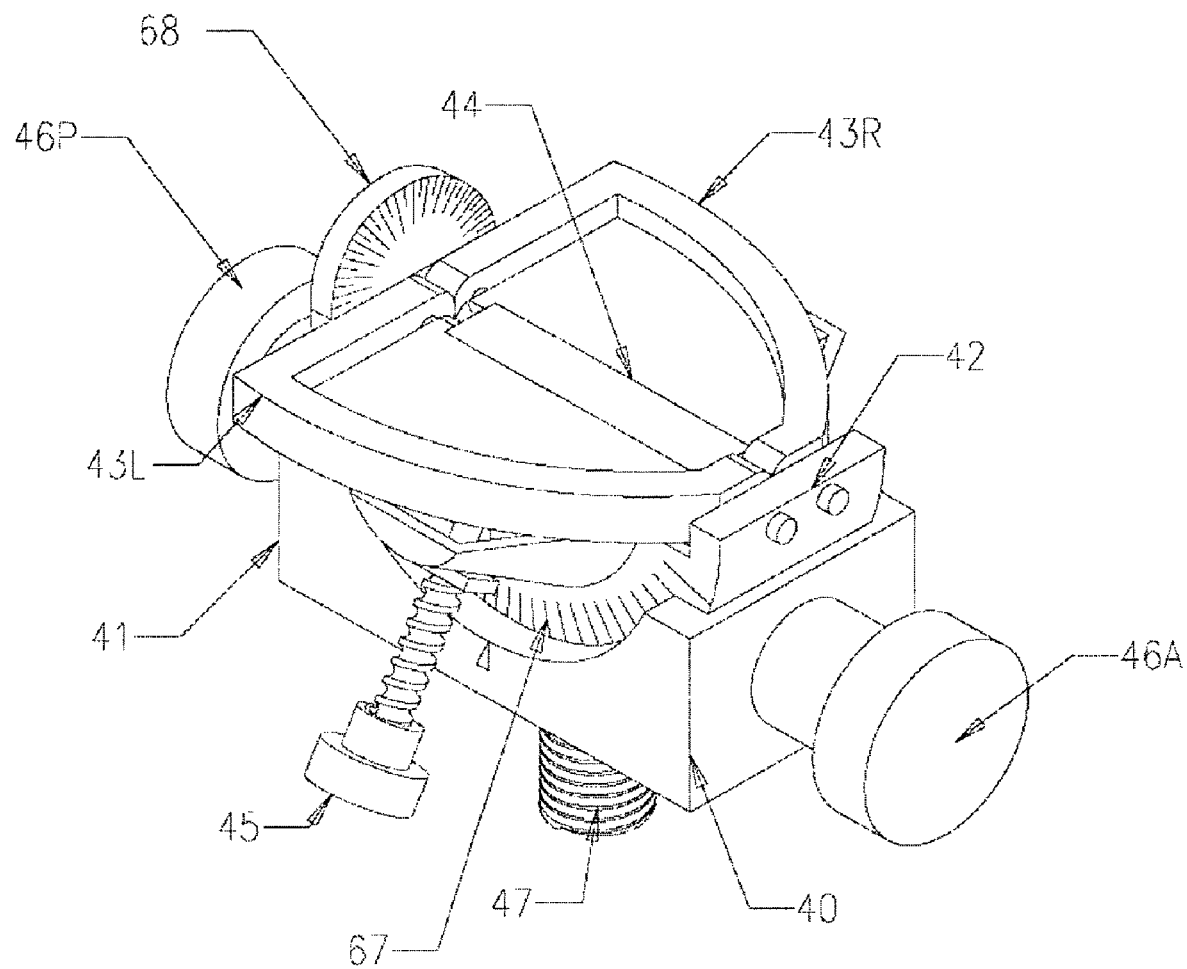
FIG. NO. 17

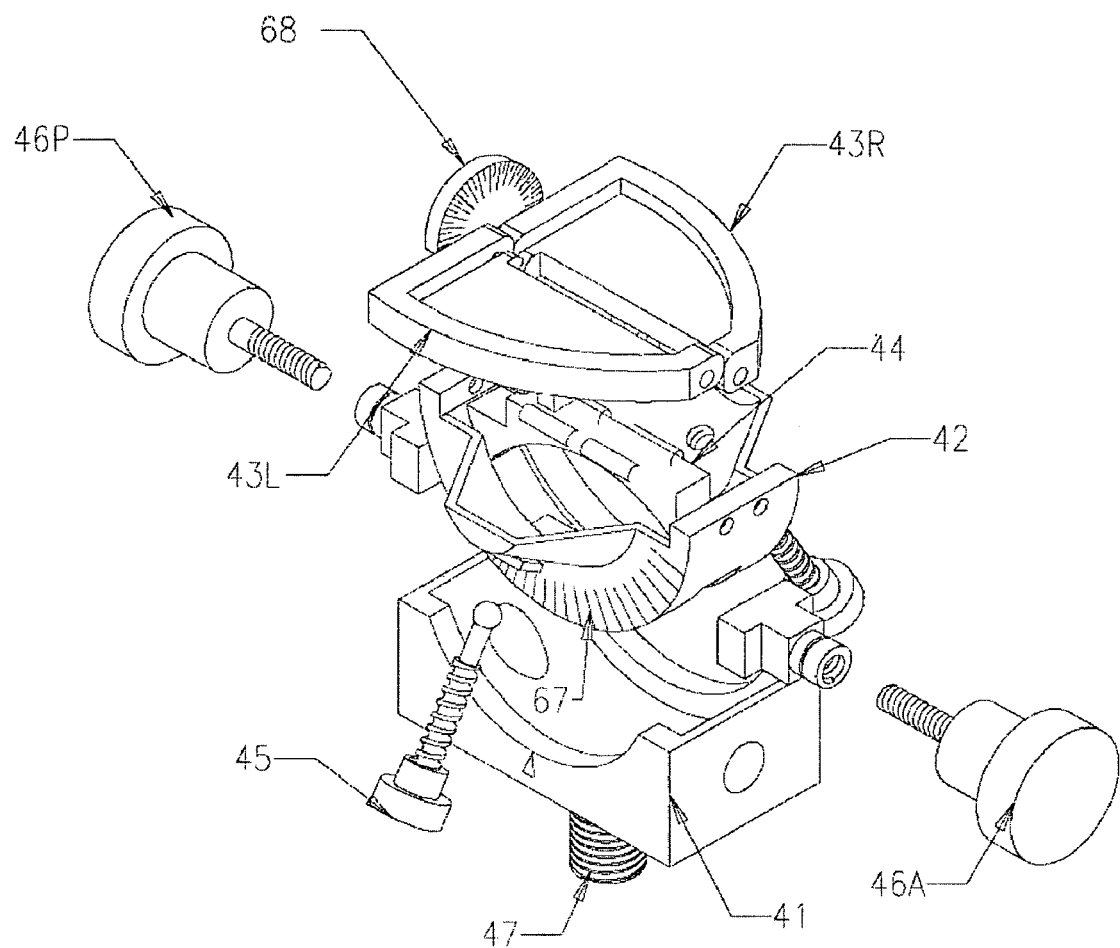
FIG. NO. 18

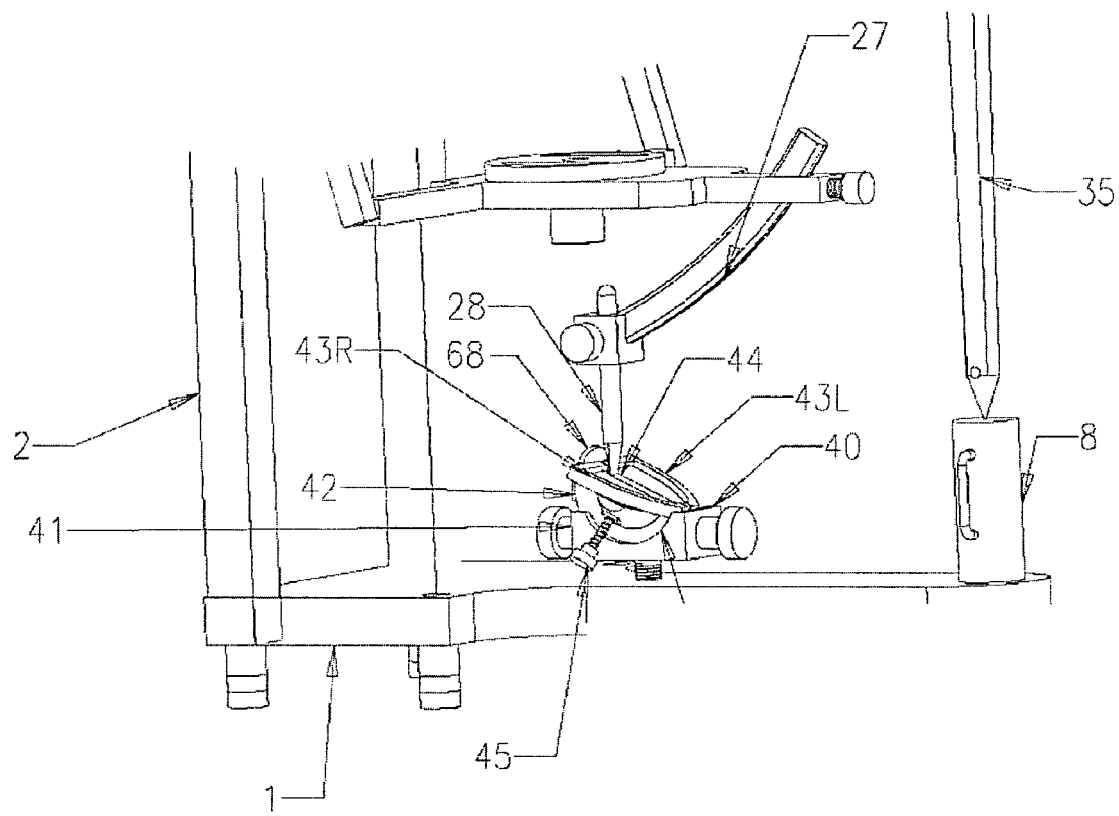
FIG. NO. 19

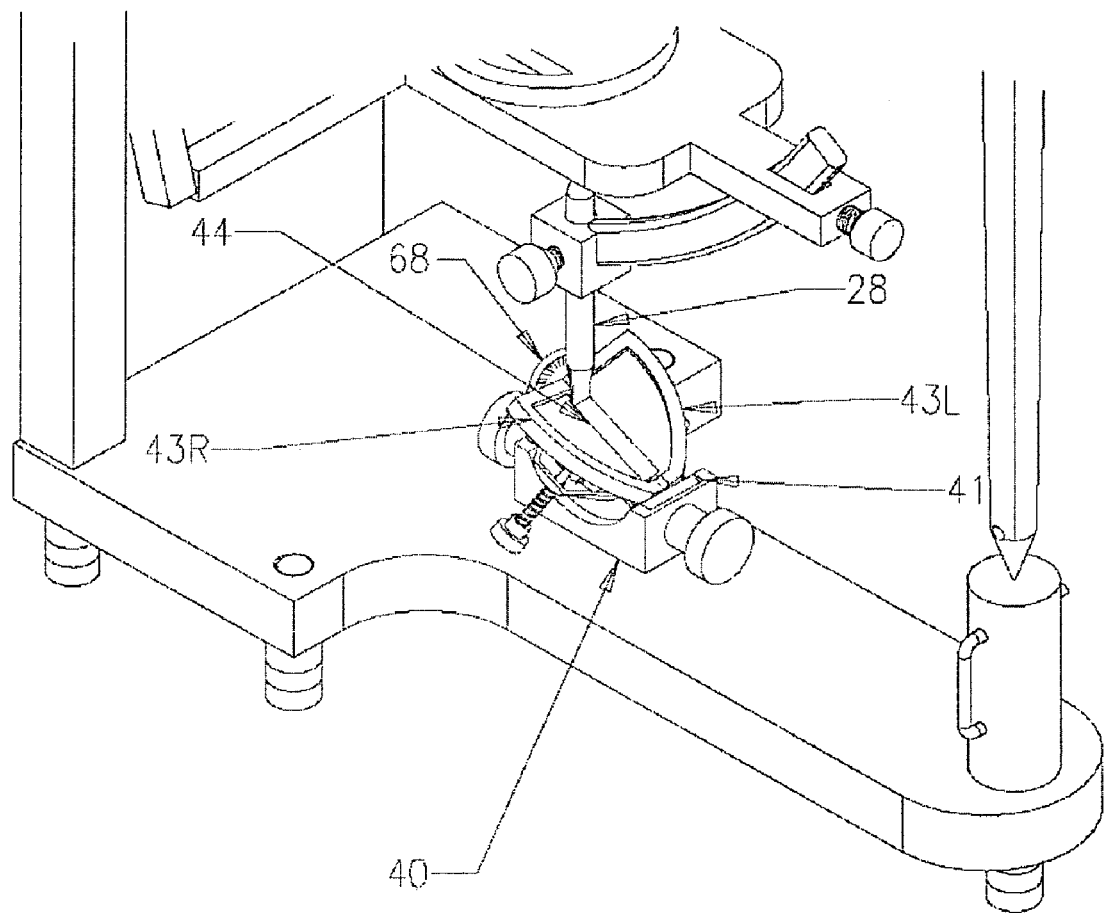
FIG. NO. 20

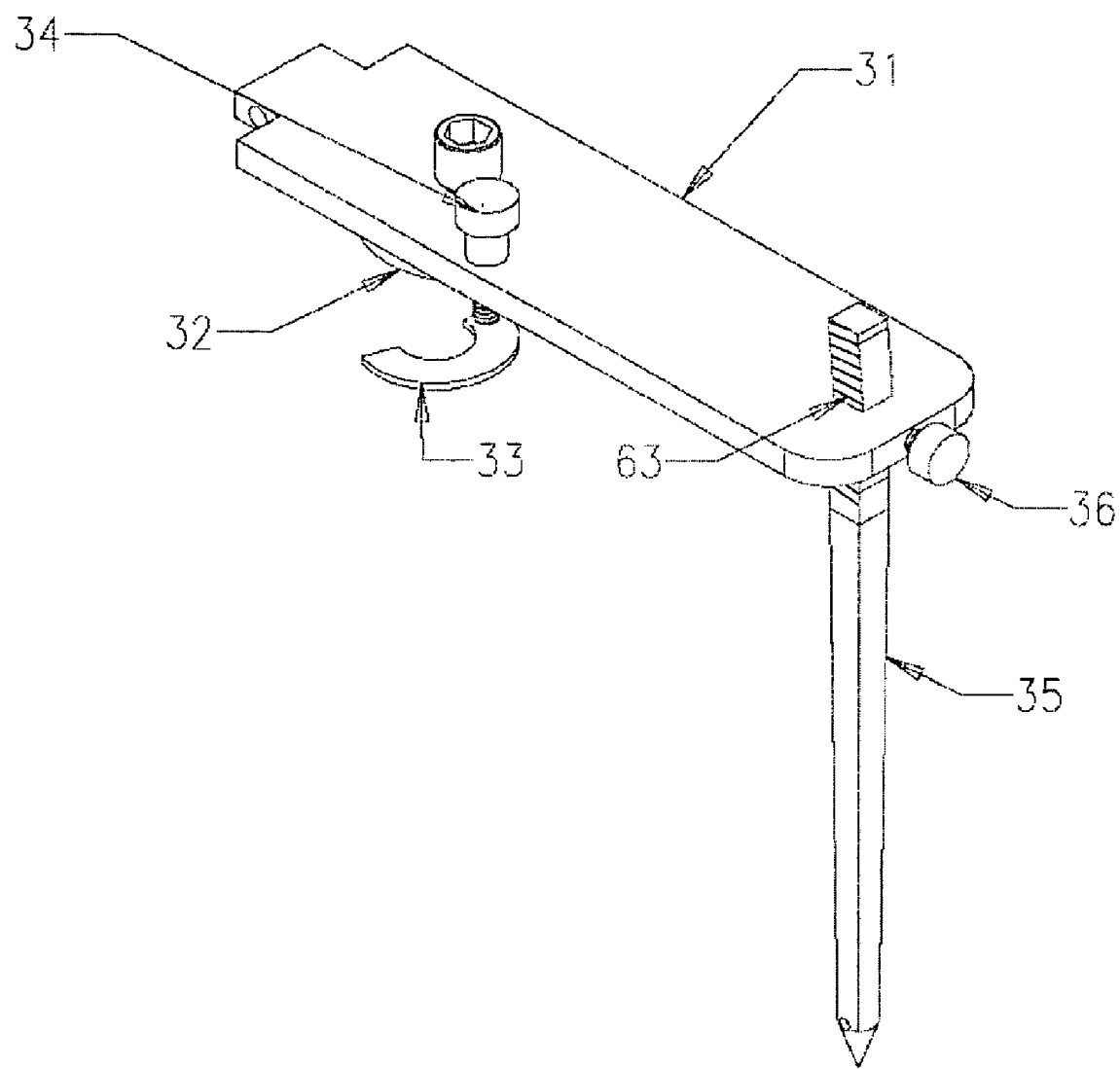
FIG. NO. 21

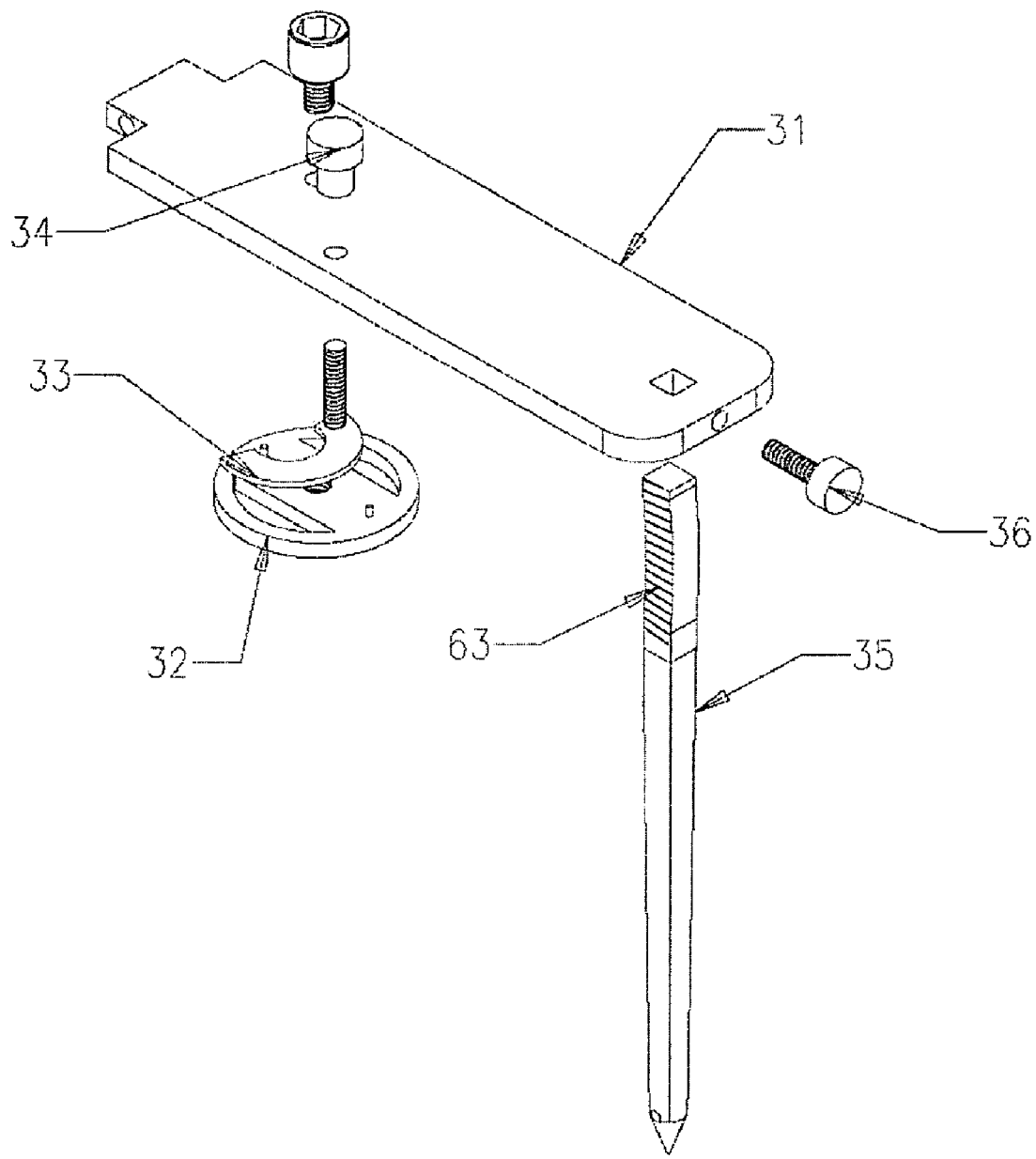
FIG. NO. 22

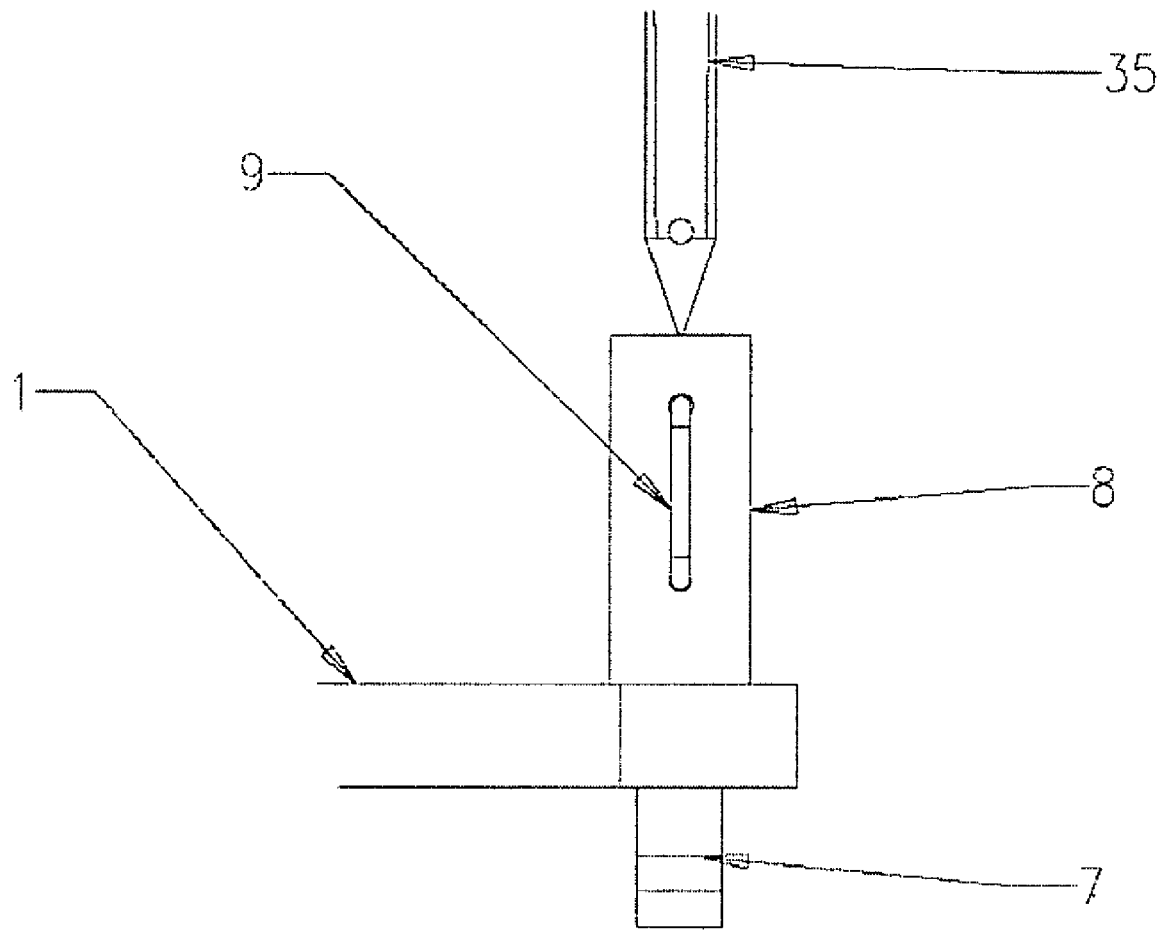
FIG. NO. 23

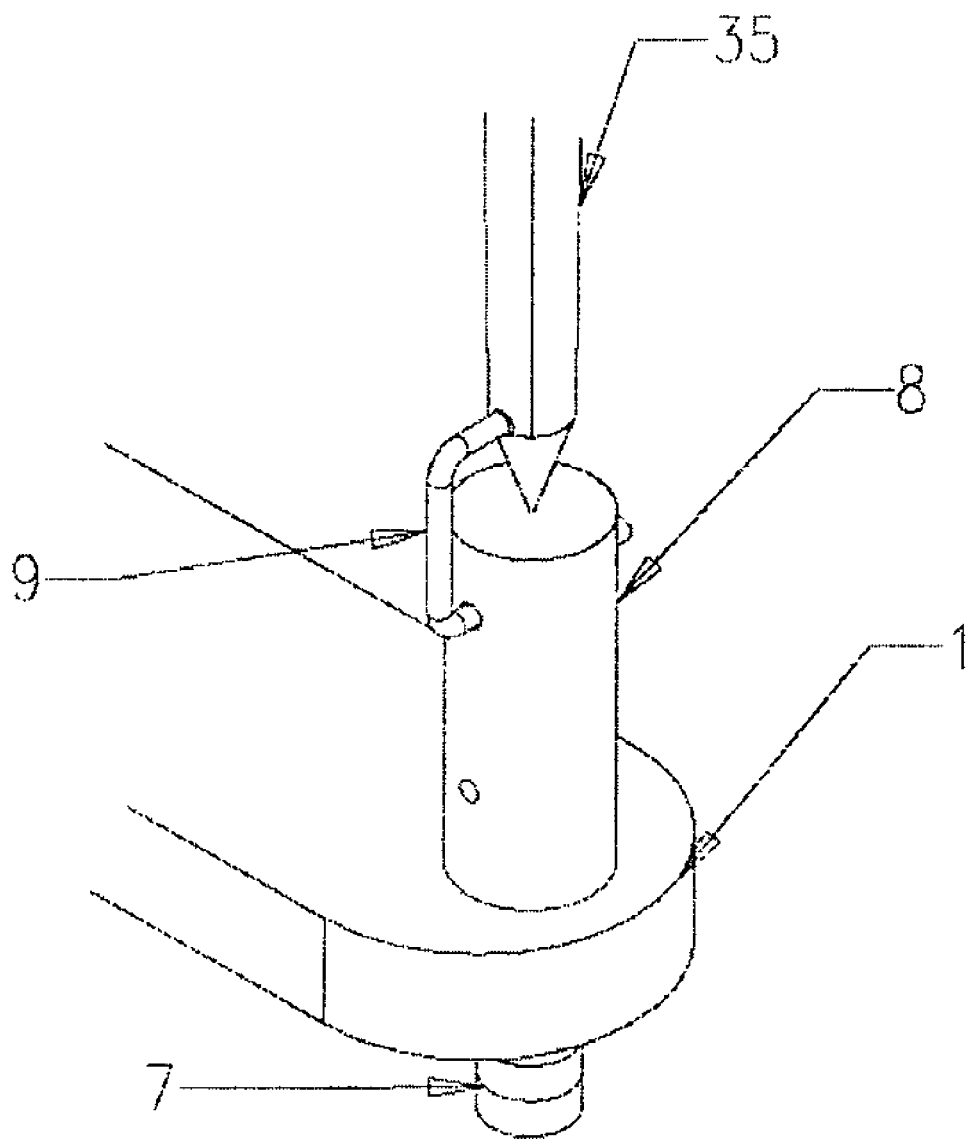
FIG. NO. 24

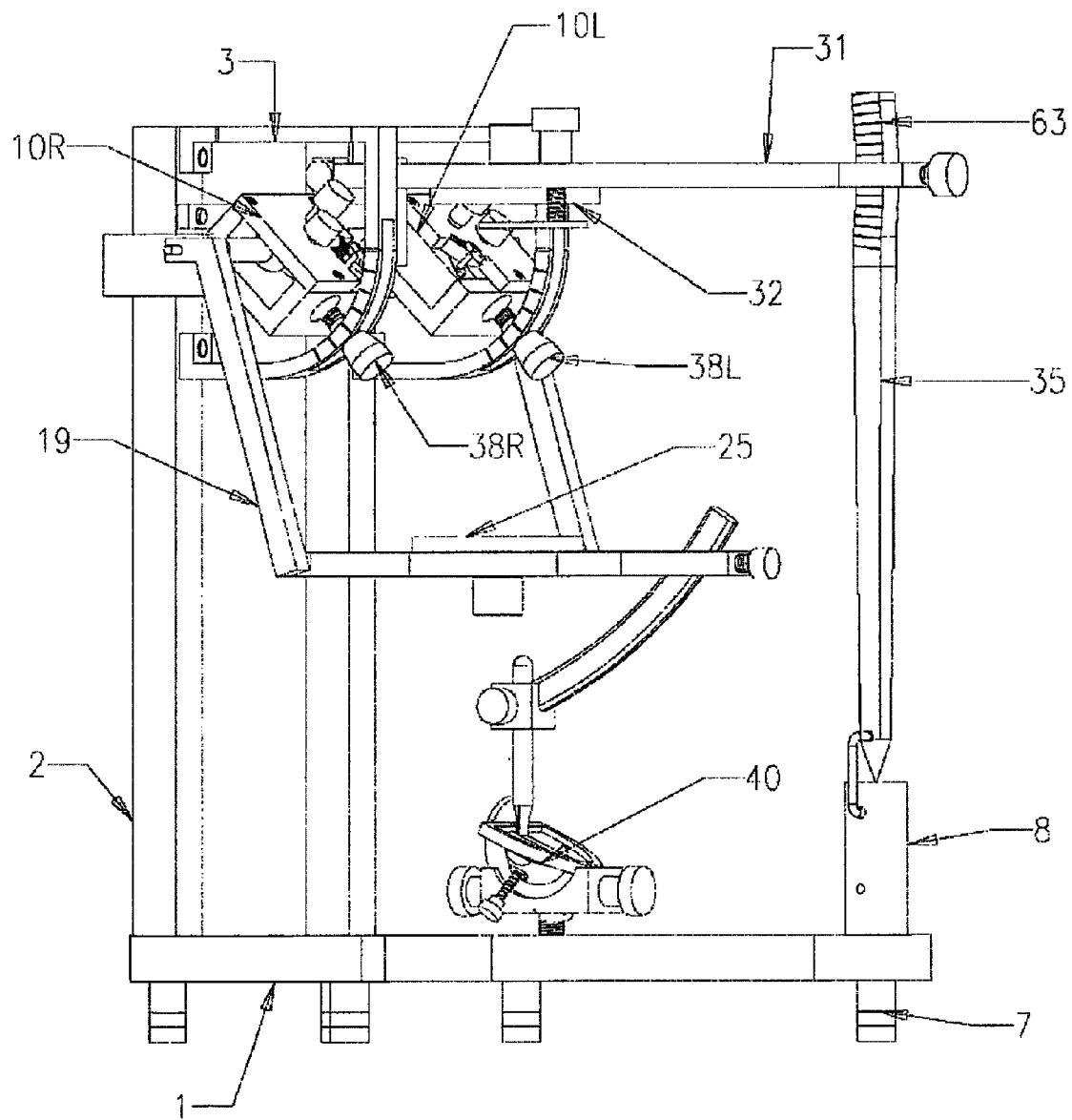
FIG. NO. 25

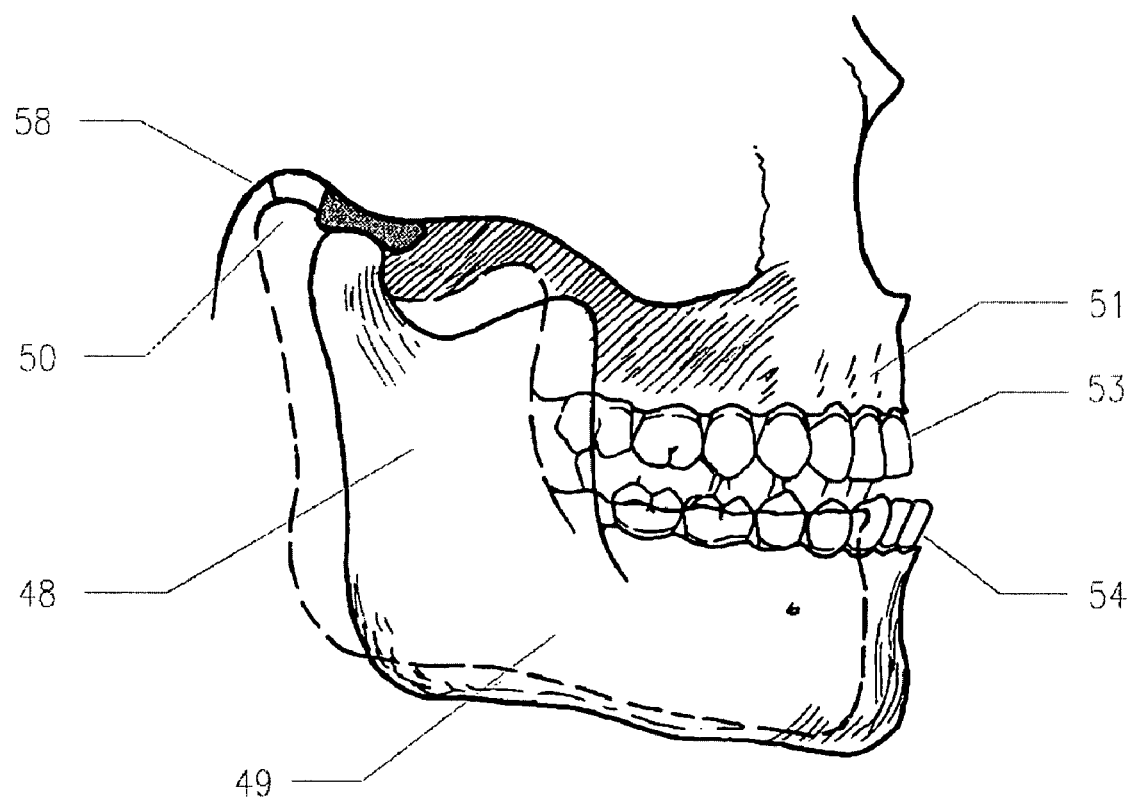
FIG. NO. 26

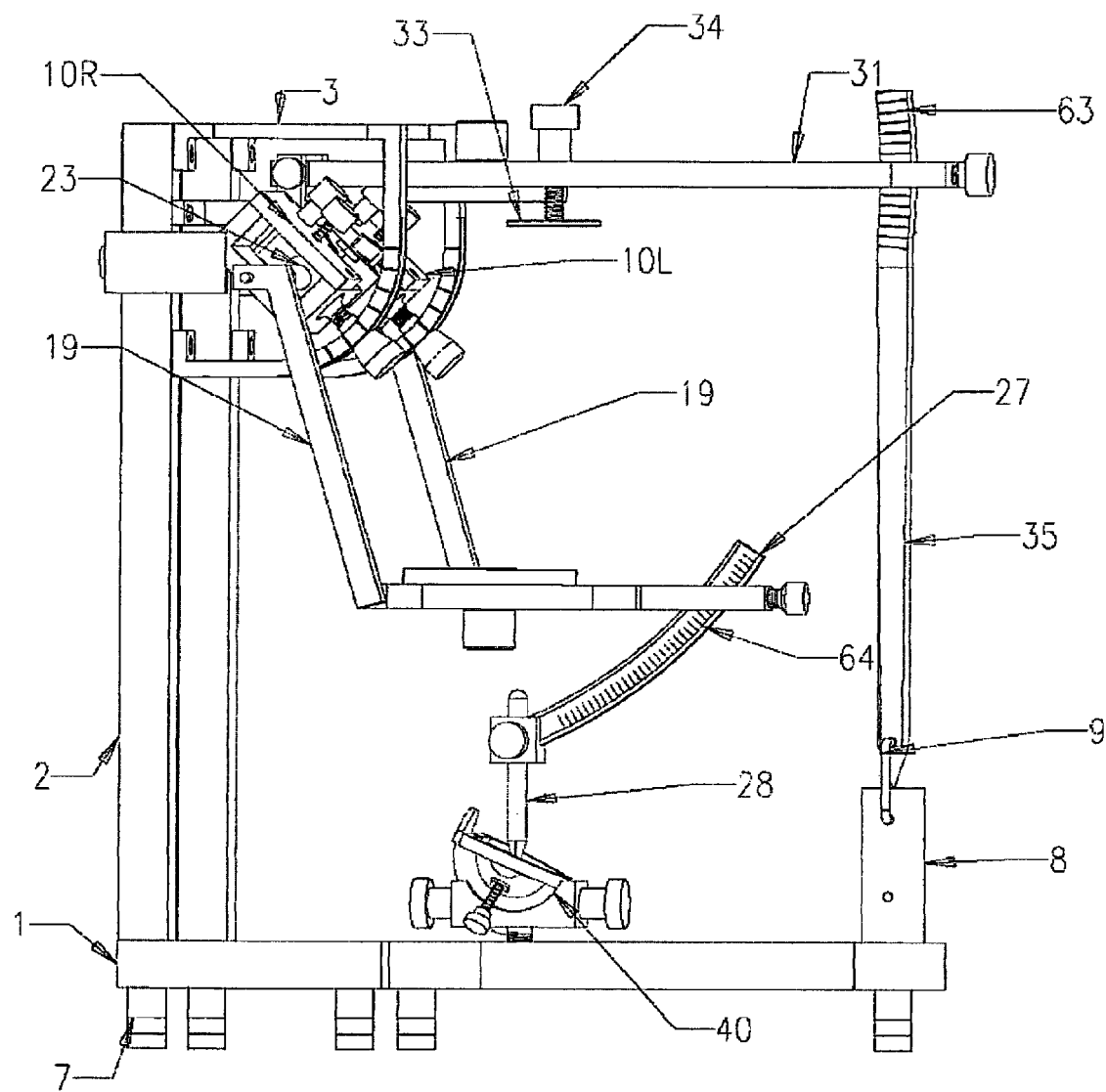
FIG. NO. 27

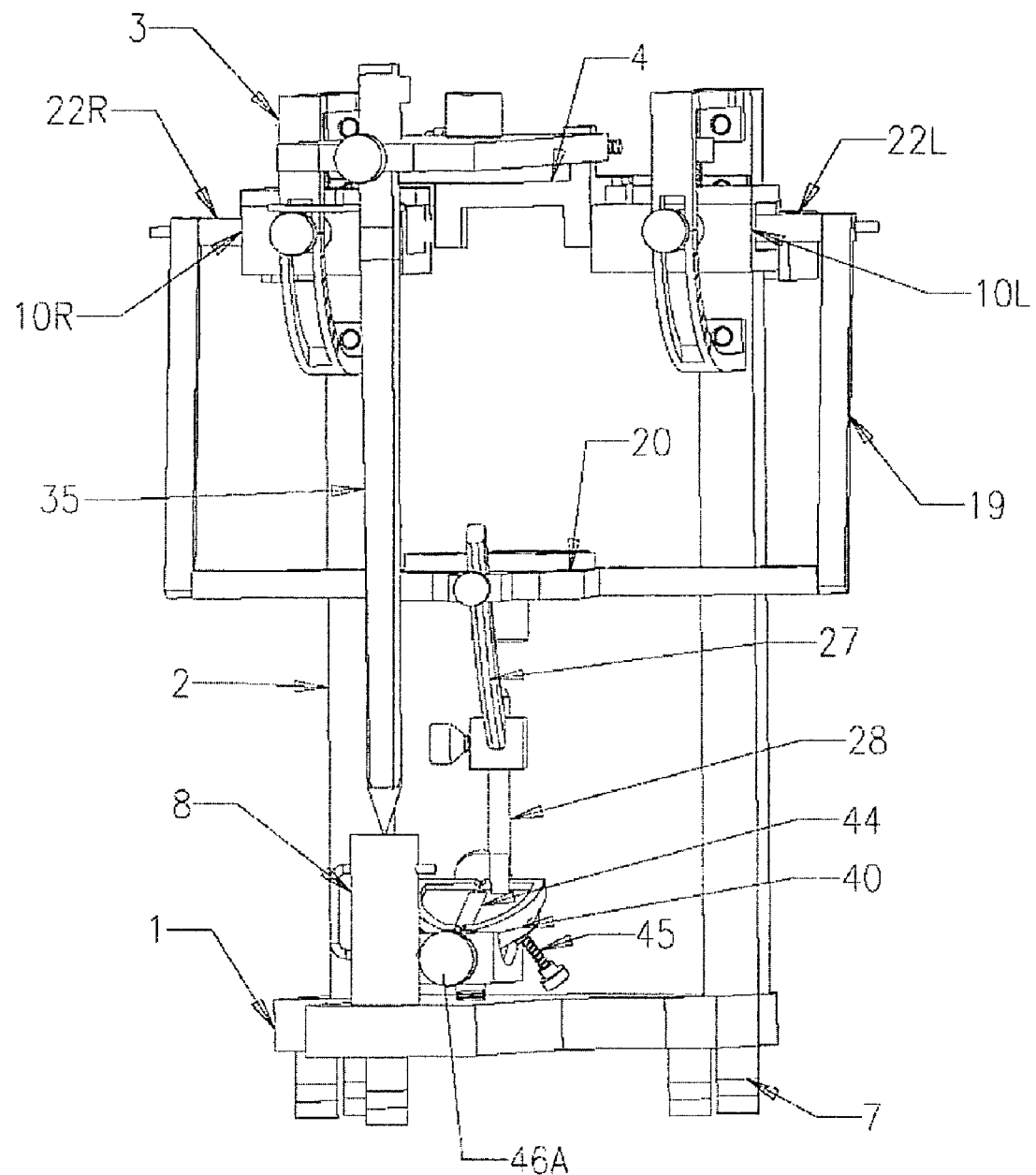
FIG. NO. 28

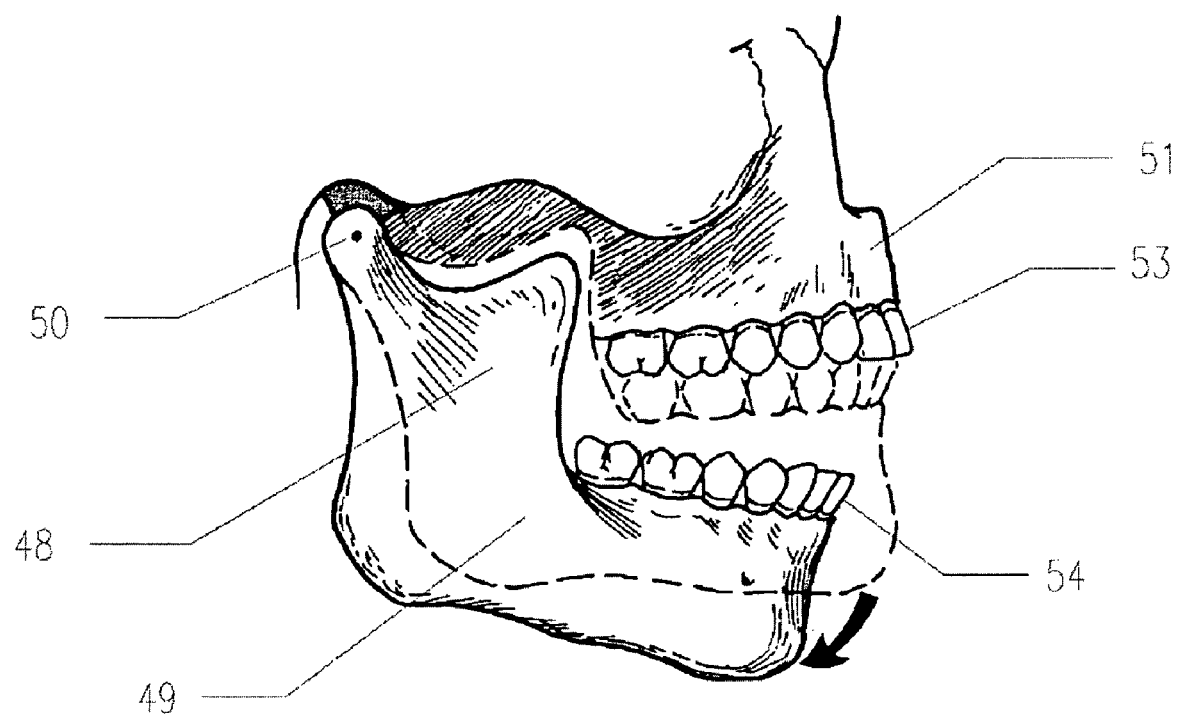
FIG. NO. 29

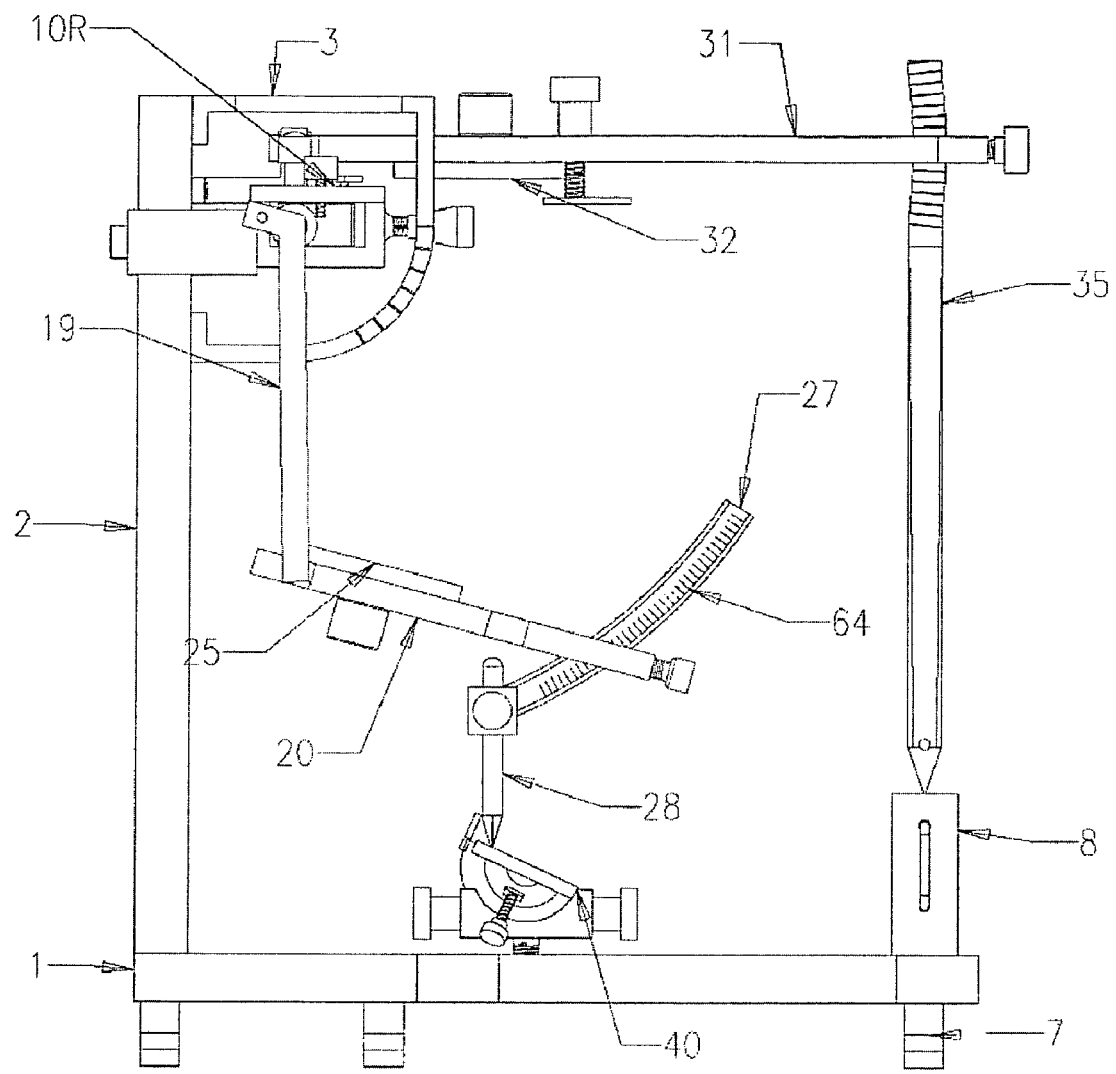
FIG. NO. 30

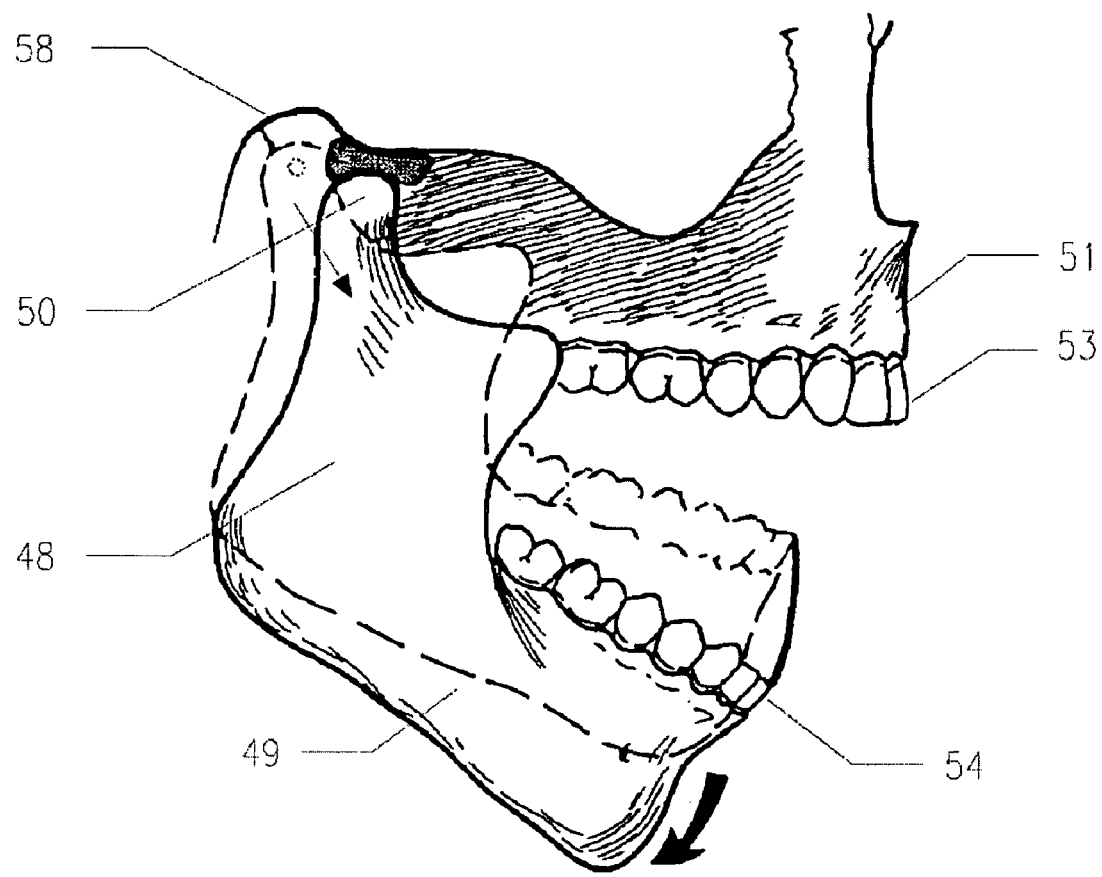
FIG. NO. 31

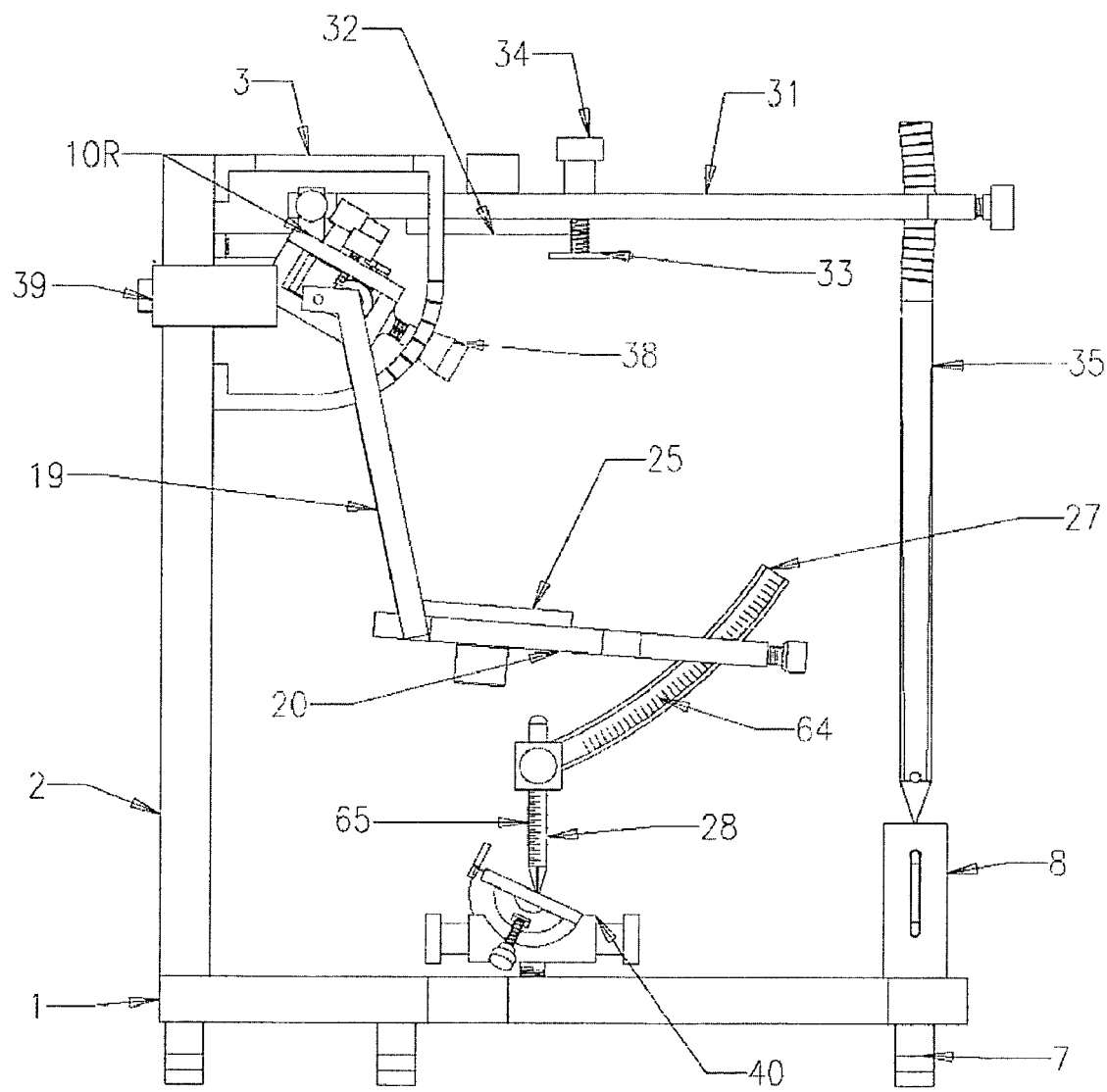
FIG. NO. 32

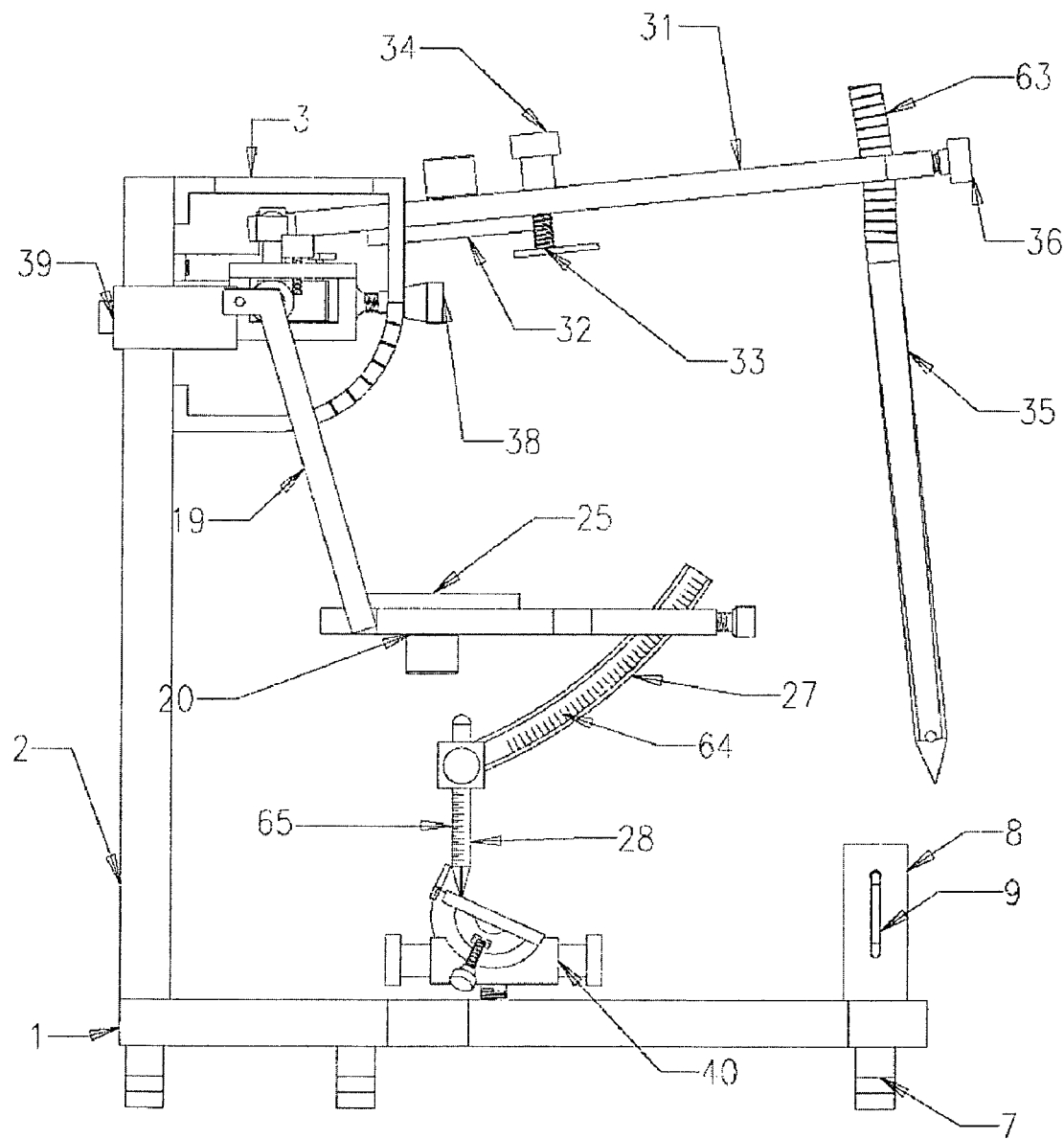
FIG. NO. 33

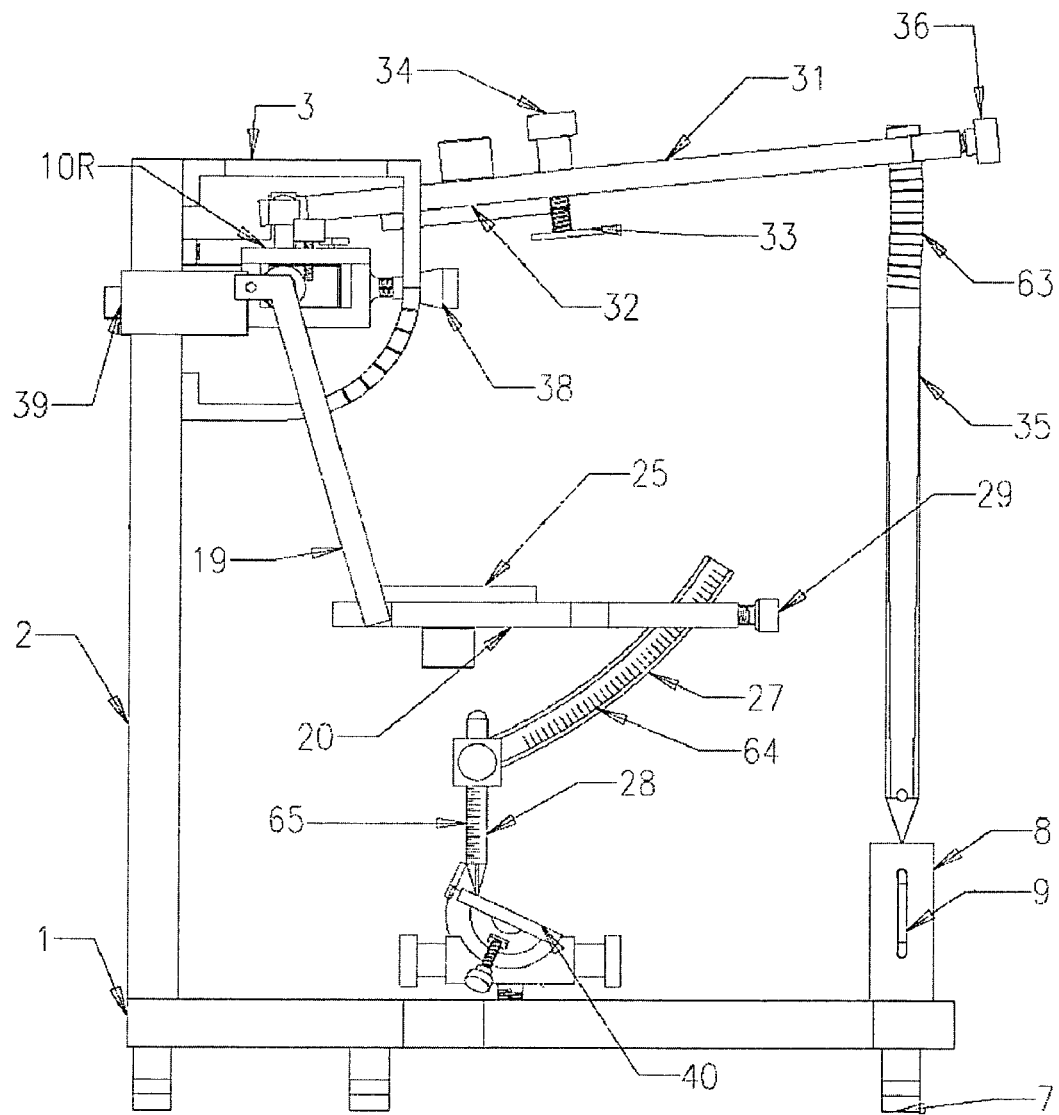
FIG. NO. 34

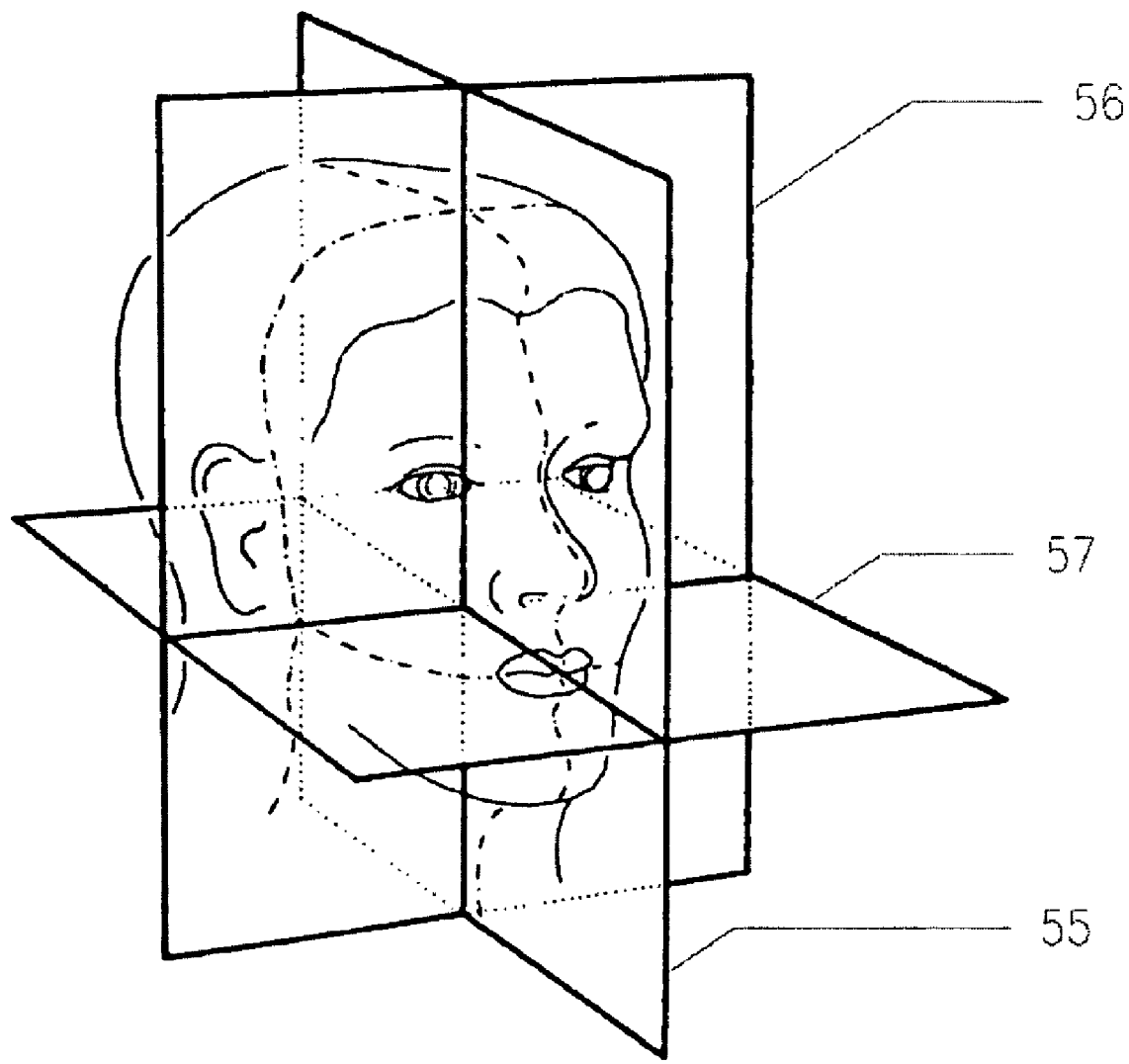
FIG. NO. 35

MOVABLE MANDIBLE ARTICULATOR

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

This invention relates to movable mandible articulator. More particularly it relates to a dental articulator capable of completely and faithfully reproducing movements of a mandibular cast and maxillary cast used for completely reproducing the human jaw movement, especially articulation in producing dental prosthesis for defective or missing teeth. Still more particularly it relates to a very simple and innovative movable mandibular articulator that duplicates the mandibular movement of the human jaw. The articulator or the present invention allows easy visualization of the mandibular movements and duplicates them by reproducing the same movements and not their mirror images. The articulator is a very versatile articulator which enables development of accurate dental occlusion. It can be utilized as an ideal education tool for explaining occlusion in dental schools as well as be utilized by the most versatile laboratories to make dental crowns, partial fixed dentures; removable dentures implant prostheses maxillofacial prostheses, and orthognathic surgical casts.

2. Description of Related Art Including Information Disclosed Under 37 CFR 1.97 and 37 CFR 1.98

The movable mandible articulator is a very simple and innovative articulator that duplicates the mandibular movement of the human jaw. It allows easy visualization of the mandibular movements and duplicates them by reproducing the same movements and not their mirror images. It is a very versatile articulator which will allows the development of accurate dental occlusion. It can be utilized as an ideal education tool for explaining occlusion in dental schools as well as be utilized by the most versatile laboratories to make dental crowns, partial fixed dentures, removable dentures and implant prostheses.

Reproduction of all mandibular movements is indispensable to production of dental prosthesis for enabling good mastication and maintaining stability of the stomatognathic system. Interocclusal movement shows highly noticeable differences among individuals. It is therefore desirable to have a dental articulator capable of completely reproducing the mandibular movements of the jaw of each individual.

A variety of dental articulators has been devised so far for this purpose. The different types of articulators such as ancient hinge type to nonarcon type to state of the art arcon type of articulators have always attempted to mimic the anatomy and movement of the mandible as closely as possible to what is effected by the human body.

In the human body, the mandible terminates at either end in a ball like condylar head which is attached to a housing called the glenoid fossa by way of muscles and ligaments which allow the movement of the mandible in all six directions i.e. protrusive, retrusive, left lateral, right lateral, vertical up and vertical down movements. The temporomandibular joint condylar ball (element) is attached to the mandible and the condylar housing is attached to the skull (maxillary part).

In the non arcon articulators the condylar head (element) is attached to the maxilla i.e. the upper member of the articulator and the condylar housing was attached to the mandible i.e. the lower member.

In the arcon articulators, the condylar element is attached to the mandibular member (lower member or base) and the condylar housing is attached to the upper member (maxillary member) thus in a static position it duplicated the human jaw. The various types of arcon articulators include 1) fully adjustable articulators
2) semi-adjustable articulators
3) set condylar path articulators
4) combination (set condylar path or fully adjustable) articulators But in all these articulators mandibular movement in the mouth is simulated by movement of the maxillary member in the articulator i.e. mandibular movement to the left side is simulated by movement of maxillary member to the right side. In dentistry, the front side and plane in a general sense are expressed in terms of "frontal plane", "sagittal plane" and "occlusal plane" respectively. In general, the side towards which mandibular movement is directed is termed the 'working side' and the opposite side is termed the 'balancing or non-working side' of the maxilla and mandible which constitute the jaw. The mandible is movable and restrained in movement via configuration of the glenoid fossa accommodating right and left "condyle heads". The mandible can move in six protrusive, retrusive, left lateral, right lateral, vertical up and vertical down movements. A center of a condylar head is termed as "condylar point" and a line connecting the centers of right and left condyle heads is termed as "condylar axis" and locus along which the condylar point moves along the glenoid fossa is termed as the "condylar path".

Jaw movements to be reproduced are fulfilled by the mandibular movement made in the five directions as thought above. However conventional articulators cannot perform all the five directional mandibular movements. For reproducing the jaw movement i.e. movement of the condylar points in the protrusive, leftward and rightward directions will suffice. With respect to the lateral movements of the jaws, when the mandible moves rightward the right condyle head works as the working side and the left condyle head works as the balancing side. The reverse is also true when the mandible moves leftwards. Thus the jaw movement to be reproduced must vary according to the movement of each condylar head which is performed in a different manner in moving the mandible right or leftward.

However, all existing articulators, even the fully adjustable ones, simulate this mandibular movement by movement of maxillary member to the opposite side.

BRIEF SUMMARY OF THE INVENTION

The articulator provided by the present invention resolves to remove any confusion by actually duplicating the jaw movements by moving the mandibular member to the respective sides in order to create the desired mandibular movement.

Another important criterion is the anterior incisal pin which creates the third point of reference (the 2 condyle points being the two posterior points)

In understanding occlusion, anterior guidance is an important factor. Anterior guidance is the path which traversed by the lower anterior teeth on the palatal slopes of the upper anterior teeth when the mandible is protruded anteriorly. This can be in a straight protrusive path, when the mandible is protruded forward straight and it can be a lateral-protrusive path when the mandible is protruded in a lateral path in the left and right lateral directions.

Now the incisal pin which is attached to the movable part i.e. to the maxillary member rests on an incisal table. The platform can be sloped anteroposteriorly and in a left and right lateral direction and corresponds to the angles created by the protrusive and lateral protrusive pathways of the mandible However, in all prior articulators, these slopes were created by the incisal pin attached to the maxillary member as only the maxillary member was movable. Hence to represent protrusion of the mandible the incisal pin along with the maxillary member was retruded and to represent lateral movement of the mandible the incisal pin along with the maxillary member was moved laterally in a direction that was reverse to that of the desired lateral movement of the mandible only in the "movable mandible articulator" since the incisal pin is attached to the mandibular member and that the mandibular member is movable the incisal guide pin is moved in the same direction and slope as the mandibular anterior teeth to create incisal guidance in a straight protrusive and laterotrusive paths.

The main object of the present invention is to provide an articulator capable of completely and faithfully reproducing movements of a mandibular cast and maxillary cast by analogy occlusion in a human—i.e. movement of mandible in a human replicated by the movement of the mandibular member holding the mandibular cast, in the articulator.

Another object is to provide the articulator having introduced a suspended mandibular member, the mandible being similar to that of in human beings. The mandible is suspended from the condyles in the glenoid fossa of the tempero mandibular joint. In the articulator of the present invention, the articulator and the mandibular member are suspended between the maxillary member and the base representing the feet or base in a human.

Still another object of the present invention is to provide the articulator with a mechanism for anterior incisal guidance by providing incisal pins attached to the mandibular member. The incisal pin attached to the mandibular member creates the anterior guidance on an incisal table resting on the base.

Yet another object is to provide the articulator, creating the possibility of the condyle executing pure rotary movement in the centric position till a vertical opening between the upper and lower jaws, after which it has to translate forward in order to rotate any further causing further vertical jaw opening. This is the only articulator capable of duplicating this movement.

Still another object is to provide the articulator which gives an opportunity to change the alignment of both maxillary and Mandibular jaws as compared to the base (that represents a plane of orientation to the base of a human on the floor). This is of importance in orthodontic surgeries wherein it may be necessary to align both maxilla (upper jaw) and the mandible (lower jaw) in relation to a plane of viewing or orientation.

The detailed features of the articulator provided by the present invention are illustrated with the help of drawings accompanying this specification which are illustrative only and should not be construed to limit the scope to the present invention in any manner.

BRIEF DESCRIPTION OF THE SEVERAL VIEWS OF THE DRAWINGS

FIG. 1 is a perspective view of movable mandible articulator.

FIG. 2 is an exploded perspective view of movable mandible articulator.

FIG. 3 is a perspective view of a base assembly.

FIG. 4 is an exploded perspective view of the base assembly.

FIG. 5 is a perspective view of the left condylar box.

FIG. 6 is a perspective view of the right condylar box.

FIG. 7 is an elevation view of the interior of the left condylar box, showing the condylar track and centric lock screw.

FIG. 8 is a perspective view of the centric mounting position, showing condyles in centric position and side shift guide at 00 angulations FIG. 9 is a perspective view of the condyles, showing left lateral movement of the mandibular member and sideshift guide at Maximum lateral angulation of 300.

FIG. 10 is a perspective view of the condyles showing right lateral movement of the mandibular member with sideshift guide at maximum lateral angulation of 300.

FIG. 11 is a front elevation view showing change in the sagittal plane angulation of condylar boxes i.e change in horizontal condylar guidance angle.

FIG. 12 side view showing change in sagittal plane angulation of condylar boxes i.e change in horizontal condylar guidance angle.

FIG. 13 is a perspective view of the middle/mandibular member assembly.

FIG. 14 is an exploded perspective view of the middle/mandibular member assembly.

FIG. 15 is a front elevation view of the mandibular incisal pin showing both angular and vertical parts.

FIG. 16 is front elevation view of the change in the vertical of the vertical part of the mandibular incisal pin.

FIG. 17 is a perspective view of the mandibular incisal table.

FIG. 18 is an exploded perspective view of the mandibular incisal table.

FIG. 19 is a perspective view of the change in incisal guidance angle in the sagittal plane.

FIG. 20 is a perspective view of the change in lateral incisal guidance angle by raising the lateral flaps.

FIG. 21 is a perspective view of the upper/maxillary member assembly.

FIG. 22 is an exploded perspective view of the upper/maxillary member assembly.

FIG. 23 is a front elevation view of the maxillary incisal pin in open position with respect to maxillary incisal table.

FIG. 24 is a perspective view of the maxillary incisal pin in lock position with respect to maxillary incisal table.

FIG. 25 is a side perspective view of the articulator in centric lock position.

FIG. 26 is another side perspective view showing protrusion of the mandible in sagittal plane.

FIG. 27 is a side view of the movable mandible articulator, showing protrusion of mandibular member in the sagittal plane.

FIG. 28 is a front elevation view of the movable mandible articulator, showing laterotrusion and lateral flaps of incisal table raised.

FIG. 29 is a side view of mandible showing pure rotation in sagittal plane.

FIG. 30 is a side perspective view of the movable mandible articulator showing pure rotation of mandibular member with condyles in the centric position.

FIG. 31 is a side perspective view of mandible showing rotation and protrusion in the sagittal plane.

FIG. 32 is a side perspective view of the movable mandible articulator showing rotation and protrusion of mandibular Member in the sagittal plane.

FIG. 33 is a side elevation view of movable mandible articulator, showing opening of the maxillary member with maxillary incisal pin displaced from its position on the incisal platform.

FIG. 34 is a side perspective view of the movable mandible articulator showing change in angulation of the maxillary member with respect to the mandibular member without change in position of the maxillary incisal pin on the incisal platform.

FIG. 35 is a perspective view of the three planes of the skull.

DETAILED DESCRIPTION OF THE INVENTION

The annex chart attached to this specification gives the description of the legends used in the drawings/specification.

Referring to FIG. 1, the movable mandible articulator capable of completely and faithfully reproducing movements of a mandibular cast and maxillary cast comprises the following parts.

1) The base assembly as illustrated in FIG. 3 comprises the main skeletal framework of the articulator consisting of a base member (1) having the two vertical columns 2(L) and 2(R) at the left and right posterior ends supporting the condylar hinge assembly (4) between them. The condylar guides 3(L) and 3(R) guide are attached to each of the vertical columns 2(L) and 2(R), and a maxillary incisal table (8) is at the anterior part of the base for the maxillary member.

2) The middle/mandibular member as described in FIG. 13 consists of a U-shaped frame (19) terminating interiorly in horizontal condylar shafts 22(L) and 22(R) and auditary pins (21L) and 21(R) exteriorly at the open ends of the U shape frame (19). The condylar shafts end in condylar balls 23(L) and 23(R) attached to it at its medial end with a provision of condylar ball screws 24(R) and 24(L), the horizontal platform (20) holding a mounting plate (25) is secured by a mounting plate bolt (26) attached at the center of the horizontal platform (20) of the U shaped frame (19). An arc shaped mandibular incisal pin (27) has one end of which locked over the other end of the arc shaped mandibular incisal pin (27), being held in a holder for the vertical part of the mandibular incisal pin (69), the holder (69) having a lock screw (30) for vertical part (28) of the mandibular incisal pin (27).

3) An upper/maxillary assembly as shown in FIG. (21) consists of an upper/maxillary member (31), a maxillary mounting plate (32) at its underside, a semicircular plate (33) for the orbital pointer held on the underside of the upper/maxillary member (31) by a locknut (34), a maxillary incisal pin (35) which is angular in the top portion, rectangular in the middle portion while terminating in a pointed tip, the angular top portion passing through angular incision and held in the said incision by a lock screw (36).

4) Condylar box assemblies 10(L) and 10(R) as shown in FIG. (5) and FIG. (9) are mirror images of each other, each assembly consisting of a rectangular box which houses the condylar balls 23(L) and 23(R), each box consisting of a top plate 11(L) and 11(R), a centric locking screw 12(L) and 12(R), side shift plate locknuts 13(L) and 13(R), condylar box lock screws 14(L) and 14(R) on each of the boxes, on the medial side is the condylar hinge plate 17(L) and 17(R) which has a slot for the condylar hinge (73). The condylar boxes pivoted on the condylar hinges allowing free rotation, and the anterior parts of the condylar hinge plates 11(L) and 11(R) are angulated medially to the extent of 300 to the vertical in the coronal plane allowing the side shift guide plates 15(L) and 15(R) to rotate medially up to an angulation of 300 in the coronal plane.

5) A mandibular incisal pin assembly as shown in FIG. (15) consists of an arc shaped mandibular incisal pin (27) which ends at one end in the holder (69) also having a vertical slot through which the vertical part of mandibular incisal pin (28) passes. The vertical part rests on the mandibular incisal table (40), a lock screw (29) passing through the horizontal platform of mandibular member (20) for locking arc part of the mandiular incisal pin (27) and a lock screw (30) passing through the holder (69) for locking vertical part (28).

6) A mandibular incisal table assembly as shown FIG. (17) consists of a mandibular incisal table (40) having a flat incisal table base (41). The flat base has a incisal table lock (47), the incisal table (40) having incisal guidance lock screws 46(A and 46(P) on the anterior & posterior sides of the incisal table (40), an incisal table body (20) holding arc shaped lateral flaps 43(L) and 43(R), a central track (44) of the incisal table (40). The lateral flaps 43(L) and 43(R) are attached to the incisal table body (42) and a flap raising screw (45) for raising or lowering lateral flaps 43(L) and 43®).

7) A condylar hinge assembly FIGS. (3&4) consists of a horizontal bar (70P) adaptably fixed on the vertical columns 2(L) and 2®). The horizontal bar (70P) supports another horizontal bar anteriorly (70A) via horizontal connector bars (72 L&R). The anterior horizontal bar (70A) is attached to the vertical bar (71 L&R) which has holes 6(L) and 6(R) for maxillary hinges at the top of the both ends and condyle hinges 5(L) and 5(R) and the bottom end.

In one of the embodiments of the present invention, the upper/maxillary member is attached at the top end of the condylar hinge assembly via a maxillary hinge pin (37). The hinge is in the same axis as that of the intercondylar axis (52) thus making it seem that both the maxilla and the mandible can hinge open and close from the same axis.

In still another embodiment FIGS. (8,9&10&14), the open ends of the U shaped frame of the middle/mandibular assembly is resting on the condylar boxes 10(L) and 10(R) through condylar balls (23L &23R) which are attached to the condyle shafts 22L & 22R by the condyle ball screws 24(L). In yet another embodiment, the condylbox lock screws 14(L) and 14(R) pass through the angular slot of the condyle guide 3(L) and 3(R) on the angular, the lock screws 14(L) and 14(R) having condyle box lock nuts 38(L) and 38(R) on the other sides of the condyle tracks 18(L) and 18®).

In another embodiment, the maxillary member (31) has the maxillary mounting plate (32) attached to its underside and a semi-circular orbital pointer (33) at a vertical height difference of ~7 mm from the center of the condylar hinges and the auditary pins 21(L) and 21®).

In still another embodiment, the incisal pin (35) is at the anterior end of the maxillary member, the incisal pin (35) being angular in the top portion, rectangular in the middle portion and terminating in a pointed tip resting on the flat maxillary incisal table platform (8) which is attached to the base member (1).

In still another embodiment, the maxillary member has an angulated incision adaptably matching the angular portion of the maxillary incisal pin (35), the angle of which is concurrent with the arc of rotation of the maxillary member (31) with its center of rotation being the maxillary hinge pin (37) allowing a vertical opening and closing of the upper/maxillary member (31) of up to ±5 mm without change in the position of the tip of the maxillary incisal pin (35) on its maxillary incisal table (8).

In yet another embodiment, the maxillary incisal pin (35) could be locked in position with the maxillary member (31) with a lock screw (36).

In still another embodiment, the condylar box assembly 10(L) and 10(R) are placed with the middle member assembly on condylar hinges 5(L) and 5(R))

Working of the movable mandible acticulator (MMA).

The MMA is a true Arcon articulator. It has 3 members—the base member (1) representing the base of a human being; an upper member (31) representing the maxilla in the skull and a middle suspended member. FIG. 13 represents the mandible that is the only suspended member of the skull.

The MMA is an Arcon articulator because the condylar spheres are attached to the mandibular member. Here the upper/maxillary member (31) is a fixed member unlike all other contemporary articulators, thus representing the maxilla (51) in the human skull as shown in FIG. 26 which is also fixed and not movable. However, in the MMA, the maxillary member (31) does have the provision of being fully opened out at 180° in order to facilitate the mounting of the maxillary dental casts.

Now, the articulator is an instrument that is supposed to simulate the maxilla and the mandible and their relationship to the opening axis of the jaws i.e. the tempero mandibular joint. Capturing this relationship in the patient is an instrument called the face bow (not described here). The face bow helps to capture the relationship of the maxilla to the tempero mandibular joint and helps to transfer this same relationship to the articulator by relating the maxillary dental cast to the condylar shafts on the articulator. The earpiece facebow is oriented via the attachment on the condylar fossa assembly to the auditary pin. So, when the earpiece facebow is mounted via the auditary pin, it orients the maxillary dental cast to the opening axis of the MMA at this stage. The upper maxillary member (31) is kept horizontal and parallel to the base member (1) and also to the floor and the vertical pin of the upper member. That is, the maxillary incisal pin (35) is locked both by the lock screw for maxillary incisal pin (36) and inferiorly by the lock pin for maxillary incisal table (9).

The auditary pin which is attached to the side of the condylar fossa assembly comes into the same plane as the intercondylar axis (52) when the horizontal platform of the mandibular member (20) is made parallel to the maxillary member (31) and the base (1).

At this stage, the condylar housing and the condylar track (18), can be kept at a horizontal inclination in the sagittal plane of 0°. The condylar fossa assembly is supported by the condyle box lock screw (14) and condyle box lock nut (38) Also the condyle balls (23) should be in contact with the rear wall, which indicates the centric position, and also in contact medially with the side shift plate (16), which also should have a 0° angulations in the axial plane i.e. the side shift should be pointing straight ahead. Once both the rear and medial contacts have been secured, the centric locking screw (12) and the side shift plate locknut (13) should be tightened respectively. The maxillary dental cast is mounted on the mounting plate of maxillary member (32) with the help of dental plaster.

Once the maxillary dental cast is mounted, the mandibular dental cast is related to it via a wax interocclusal record. The condylar shafts are retained in the same position. The arc part of mandibular incisal pin (27) is kept at the 0 mark which makes the middle/mandibular member parallel to both the upper and the base members. The mandibular dental cast is mounted in this position on the mounting plate of mandibular member (25) with the help of dental plaster.

In the centric lock position the horizontal platform of the mandibular member (20) along with the mandibular dental cast can freely rotate open upto a vertical opening of 20 mm. This amount of interocclusal separation corresponds to the human mandible which can purely open upto a vertical opening of 20 mm. Beyond this the condyle has to translate forward. Similarly, in the MMA, in the centric position the middle/mandibular member can purely rotate up to 20 mm. Beyond this, the movement is restricted by the vertical column (2) for any further opening the centric locking screws (12 L & R) on both sides should be loosened. This allows the condylar balls on both sides to translate forward along the condylar tracks (18) which gives the possibility of further rotation if required.

When the centric locking screw (12) is loosened on either side, and the sideshift guide is kept at 0 degree angulations i.e pointing straight ahead, the condylar balls on both sides translate forward along the condylar tracks. At this point, the vertical part of the mandibular incisal pin (28) is resting on the mandibular incisal table (40) and can glide forward in protrusive movement. So, though the middle/mandibular member (19 & 20) is a suspended member, because of the triangular point contact i.e 2 posterior contacts at the condylar balls (23 L & R) on the condylar tracks (18 L & R) and 1 anterior contact point of the mandibular incisal pin (28) on the mandibular incisal table (40), it is stable in all ranges of mandibular movement.

When the side shift plate locknut (13) is loosened it allows for medial movement of the condylar shaft. Now, since both the condylar shafts are linked to each other via the linkage to the middle/mandibular member, The medial/inward movement of the condylar shaft on one side causes lateral or outward movement of the contra lateral condylar element and to the same extent. thus we have the terminology of working and nonworking/balancing condyle. The working condyle is considered the condylar element towards which the other condylar element moves. Thus, if the left condylar element moves inward/medially, It is termed as the nonworking/balancing condyle and the right condylar element which moves outward/lateral is termed the working condyle.

So, in a human being, if the mandible has to make a lateral movement to the left side, then the left side condyle becomes the working condyle and the right condyle becomes the nonworking condyle. In this case, the right condyle comes downward and medially along the medial slopes of the glenoid fossa towards the left side. Meanwhile, the left condyle pivots in its place and almost acts as a center of a circle while its distance to the other condyle becomes the radius thus making the mandible move to the left along an arc.

Similarly in the MMA FIG. (9), in order to move the middle/mandibular member (20) to the left, the centric locking screws (12 L & R) are loosened. Also, the right side side-shift plate (16R) can be adjusted up to a medial angulation of up to 30 degrees to allow the right side condylar shafts to guide on the condylar tracks (18 R) in a medial direction towards the left side. Thus, the left condylar element becomes the working side condyle and the right side condylar element becomes the non-working side condyle showing medial and forward translation.

The same movement can be performed in order to produce right sided movement of the middle/mandibular member FIG. (10). Thus the MMA can duplicate the movements of the mandible in a human by making the same movements of the mandibular member.

Now after the maxillary and mandibular dental casts have been mounted on their respective members, interocclusal records can be obtained which can be utilized in order to obtain the horizontal condylar guidance angle of each side and also the side shift guide of each side.

The incisal pin (27, 28) attached to the mandibular member is also unique. For the first time, an incisal pin attached to the mandibular member is used to create the incisal or anterior guidance of occlusion in previous articulators. This was not possible as the mandibular member was the stationary member. However, the MMA duplicates the human jaw and occlusion in order to create the anterior guidance. The incisal table that creates the third point of the stable tripod can be of a mechanical type, wherein the angulations can be changed in both the anteroposterior and sideways direction (lateral direction) or it can be customized to the existing occlusion of the mounted dental casts. The incisal pin is unique in the sense that it is arc shaped in the top half (27) and vertical in the bottom half (28). The arc of curvature of the arced incisal pin (27,) is the same as part of the circumference of a circle with the intercondylar axis (52) as the center and the distance to the middle of the arc shaped mandibular incisal pin (27). Thus, whenever the level of the middle/mandibular member is raised or lowered in order to raise or lower the vertical dimension, the incisal point of the apex will not move from its position of contact on the incisal table. Also the vertical mandibular incisal pin (28) allows free opening movement of the middle/mandibular member. Once the vertical dimension of the middle/mandibular member is fixed by the lock screw for arc part of mandibular incisal pin (29) the level need not be touched or changed in order to allow full opening of the mandibular member. Ordinarily, on full opening the mandibular member, the incisal pin would have obstructed this free arc of rotation downwards but as the vertical part of the incisal pin can be raised or lowered to allow the free rotation. Since the vertical part can be adjusted (65), on loosening the lock screw (30), the original height of the incisal pin is restored, and it can be returned back to its same position on the incisal table. This allows the existing vertical dimension to be restored to the same level. The angulations on the incisal table can be changed by the incisal guidance lock screws (46A&P) at the bottom of the base member.

The main advantages of the MMA provided by the present invention are as follows:

1. This is the first articulator that duplicates the movement of the lower jaw i.e the mandible. This is the only articulator that allows movement of the mandibular member to represent mandibular movement in the patient and not the reverse movement of the maxillary member of the articulator.
2. This is a true Arcon articulator.
3. This articulator is ideal for education, clinical and laboratory use.
4. The MMA. can allow increase or decrease of the vertical dimension of either and/or the mandibular/maxillary members.
5. The vertical dimension of the mandibular and the maxillary members can be changed without change in the position of their respective incisal pins on their corresponding incisal tables.
6. This the first articulator with a separate incisal pin along with its own incisal table for the mandibular and maxillary members.

ANNEX CHART

| NUMBER OF THE LEGEND | NOMENCLATURE/DESCRIPTION |
|---|---|
| 1 | Base member |
| 2 | Vertical column-L & R |
| 3 | Condyle guide-L & R |
| 4 | Condyle Hinge assembly |
| 5 | Condyle Hinge-L & R |
| 6 | Hole for maxillary hinge pin |
| 7 | Stands |
| 8 | Maxillary incisal table |
| 9 | Lock pin for Maxillary incisal table |
| 10 | Condyle box-L & R |
| 11 | Top plate of Condyle box-L & R |
| 12 | Centric locking screw-L & R |
| 13 | Sideshift plate locknut-L & R |
| 14 | Condyle box lock screw-L & R |
| 15 | Sideshift plate marker-L & R |
| 16 | Sideshift plate-L & R |
| 17 | Condyle Hinge plate-L & R |
| 18 | Condylar track |
| 19 | Vertical component of mandibular member |
| 20 | Horizontal platform of mandibular member |
| 21 | Auditary pin-L & R |
| 22 | Condyle shaft-L & R |
| 23 | Condyle ball-L & R |
| 24 | Condyle ball screw-L&R |
| 25 | Mounting plate of mandibular member |
| 26 | Mounting plate bolt |
| 27 | Arc part of mandibular incisal pin |
| 28 | Vertical part of mandibular incisal pin |
| 29 | Lock screw for arc part of mandibular incisal pin |
| 30 | Lock screw for vertical part of mandibular incisal pin |
| 31 | Upper/maxillary member |
| 32 | Mounting plate of the maxillary member |
| 33 | Plate for the orbital pointer |
| 34 | Lock nut for the plate for the orbital pointer |
| 35 | Maxillary incisal pin |
| 36 | Lock screw for maxillary incisal pin |
| 37 | Maxillary hinge pin |
| 38 | Condyle box lock nut-L & R |
| 39 | Lateral stopper for condyle box-L & R |
| 40 | Mandibular incisal table |
| 41 | Incisal table base |
| 42 | Incisal table body |
| 43 | Lateral flap of incisal table-L & R |
| 44 | Central track of incisal table |
| 45 | Flap raising screw |
| 46 | Incisal guidance lock screw-A&P |
| 47 | Incisal table lock |
| 48 | Ramus of mandible |
| 49 | Body of mandible |
| 50 | Condylar head of mandible |
| 51 | Maxilla |
| 52 | Intercondylar axis |
| 53 | Maxillary teeth |
| 54 | Mandibular teeth |
| 55 | Median sagittal plane |
| 56 | Coronal plane |
| 57 | Horizontal plane |
| 58 | Glenoid fossa |
| 59 | Graduations on the side if the maxillary member |
| 60 | Side graduations for horizontal condylar guidance angle-L & R |
| 61 | Front graduations for horizontal condylar guidance angle-L & R |
| 62 | Graduations for lateral condylar guidance angle-L & R |
| 63 | Graduations on the maxillary incisal pin |
| 64 | Graduations on the angular part of mandibular incisal pin |
| 65 | Graduations on the vertical part of mandibular incisal pin |
| 66 | Graduations on the horizontal platform of mandibular member |
| 67 | Graduations for the sagittal incisal guidance angle |
| 68 | Graduations for the lateral incisal guidance angle |
| 69 | Holder for the vertical part of mandibular incisal pin |
| 70 | Horizontal bar of condyle hinge assembly-A&P |
| 71 | Vertical bar of condyle hinge assembly-L&R |

ANNEX CHART-continued

| NUMBER OF THE LEGEND | NOMENCLATURE/DESCRIPTION |
|---|---|
| 72 | Connector bar of condyle hinge assembly-L&R |
| 73 | Slot for condyle hinge-L&R |

I claim:

1. A movable mandible articulator apparatus for reproducing movements of a mandibular cast and a maxillary cast, said apparatus comprising:

a base assembly having a main skeletal framework, said base assembly having a base member with a pair of vertical columns at respective left and right posterior ends thereof, said pair of vertical columns supporting a condylar hinge assembly therebetween, said pair of vertical columns having a first condylar guide and a second condylar guide respectively attached thereto, said base assembly having a maxillary incisal table at an anterior portion of said base member;

a middle mandibular member having a U-shaped frame terminating interiorly in a pair of horizontal condylar shafts, said U-shaped frame having a pair of auditary pins extending exteriorly at respective open ends of said U-shaped frame, said pair of condylar shafts having respective condylar balls at medial ends thereof, said condylar balls being attached to said pair of condylar shafts respectively by a pair of condylar ball screws, said middle mandibular member having a horizontal platform on said U-shaped frame, said horizontal platform holding a mounting plate at a center thereof, said horizontal platform having an incision on an anterior extension thereof, said middle mandibular member having an arc-shaped mandibular incisal pin with an end held by a lock screw in said incision, said arc-shaped mandibular member having another end held within a holder, said holder housing a vertical portion of said incisal pin, said holder having a lock screw secured to said vertical portion of said incisal pin;

an upper maxillary assembly having an upper maxillary member with a maxillary mounting plate at an underside thereof, said underside of said upper maxillary member having a semicircular plate for an orbital pointer secured thereto by a locknut, said upper maxillary assembly having a maxillary incisal pin with an angular top portion and a rectangular middle portion and a pointed tip at a terminal end thereof, said angular top portion passing through said incision and secured thereto by a lock screw; and a pair of condylar box assemblies each being a mirror image of the other, each of said pair of condylar box assemblies being a rectangular box which houses said condylar balls, each of said pair of condylar boxes having a top plate and a central locking screw and side shift locknuts and condylar box lock screws thereon, the condylar box having a condylar hinge plate on a medial side thereof, said condylar hinge plate having a slot receiving said condylar hinge therein, said pair of condylar boxes being on the respective condylar hinges, said condylar hinge plate extending angularly by up to 300° to vertical in a coronal plane so as to allow said side shift guide plates to rotate up to 300° in the coronal plane.

2. The apparatus of claim 1, said upper maxillary member attached to a top end of said condylar hinge by a maxillary hinge pin.

3. The apparatus of claim 1, said open ends of said U-shaped frame of said middle mandibular assembly being attached to the condylar box through the condylar ball screws.

4. The apparatus of claim 1, said condylar box lock screws passing through said slots in the respective condylar guides, said condylar box lock screws having said condylar box lock nuts on a side of said condylar guides.

5. The apparatus of claim 1, said upper maxillary member having said maxillary mounting plate and said semicular plate at a vertical height difference of approximately 7 millimeters from said condylar hinges.

6. The apparatus of claim 1, said incisal pin being at an anterior end of said upper maxillary member, said base member having a flat maxillary incisal table platform attached thereto, said incisal pin resting on said flat maxillary incisal table platform.

7. The apparatus of claim 6, said upper maxillary member having an angular surface matching said angular top portion, said upper maxillary member having a center of rotation at said maxillary hinge pin so as to allow a vertical opening and closing of said upper maxillary member without a change in a position of said pointed top of said mandibular incisal pin of said flat maxillary incisal table platform.

8. The apparatus of claim 1, said maxillary incisal pin being locked by a locking screw with said upper maxillary member.

9. A mandibular incisal pin assembly comprising:

a mandibular incisal pin of an arch shape and having a holder at one end thereof, said holder having a vertical slot through which a vertical portion of mandibular incisal pin passes, said vertical portion resting on a mandibular incisal table, said mandibular incisal pin having a lock screw connected thereto, said holder having another lock screw passing therethrough so as to lock said vertical portion of said mandibular incisal pin;

a table assembly having a table with a flat base, said flat base having an incisal table lock, said table having guidance lock screws on lateral sides thereof, said table assembly having a pair of arc-shaped lateral flaps, said table having a central track, said pair of arc-shaped lateral flats attached to said table, said table assembly having a screw for raising or lowering said pair of arc-shaped lateral flaps; and a condylar hinge assembly having a posterior horizontal bar adaptably fixed to vertical columns, said posterior horizontal bar supporting an anterior horizontal bar, said posterior horizontal bar and said anterior horizontal bar being connected by connector bars, said anterior horizontal bar having a pair of vertical bars on opposite sides thereof, said pair of vertical bars having superior ends and inferior ends, said superior ends of said pair of vertical bars having a hole receiving a maxillary hinge pin therein, said interior ends of said vertical bars projecting a condylar hinge of said condylar hinge assembly laterally.

* * * * *